US006943353B2

(12) United States Patent
Elmore et al.

(10) Patent No.: US 6,943,353 B2
(45) Date of Patent: Sep. 13, 2005

(54) SIMULTANEOUS MULTI-BEAM PLANAR ARRAY IR (PAIR) SPECTROSCOPY

(75) Inventors: Douglas L. Elmore, Bartlett, TN (US); John F. Rabolt, Greenville, DE (US); Mei-Wei Tsao, Wilmington, DE (US)

(73) Assignee: UD Technology Corporation, Newark, DE (US)

( * ) Notice: Subject to any disclaimer, the term of this patent is extended or adjusted under 35 U.S.C. 154(b) by 29 days.

(21) Appl. No.: 10/708,927

(22) Filed: Apr. 1, 2004

(65) Prior Publication Data

US 2004/0195511 A1 Oct. 7, 2004

Related U.S. Application Data

(63) Continuation of application No. PCT/US02/08346, filed on Mar. 19, 2002, which is a continuation-in-part of application No. 09/984,137, filed on Oct. 29, 2001, now Pat. No. 6,784,428, which is a continuation of application No. PCT/US01/30724, filed on Oct. 1, 2001.

(51) Int. Cl.[7] .............................................. G01N 21/35
(52) U.S. Cl. ................................................. 250/339.02
(58) Field of Search .................................... 250/339.02

(56) References Cited

U.S. PATENT DOCUMENTS

| | | |
|---|---|---|
| 3,880,523 A | 4/1975 | Thomas |
| 4,678,332 A | 7/1987 | Rock et al. |
| 4,691,110 A | 9/1987 | Nebe |
| 4,956,555 A | 9/1990 | Woodberry |
| 5,002,392 A | 3/1991 | Swope |
| 5,157,258 A | 10/1992 | Gunning, III et al. |
| 5,371,358 A | 12/1994 | Chang et al. |
| 5,377,003 A | 12/1994 | Lewis et al. |
| 5,444,236 A | 8/1995 | Ludington et al. |
| 5,491,344 A | 2/1996 | Kenny et al. |
| 5,519,219 A | 5/1996 | Alexay et al. |
| 5,528,368 A | 6/1996 | Lewis et al. |
| 5,539,518 A | 7/1996 | Bennett |
| 5,828,450 A | 10/1998 | Dou et al. |
| 6,031,233 A | 2/2000 | Levin et al. |
| 6,204,919 B1 | 3/2001 | Barshad |
| 6,236,508 B1 | 5/2001 | Stapelbroek |
| 6,355,930 B1 | 3/2002 | Sivathanu et al. |
| 6,483,112 B1 | 11/2002 | Lewis |
| 2001/0028036 A1 * | 10/2001 | Thundat et al. ........ 250/339.02 |

FOREIGN PATENT DOCUMENTS

| | | |
|---|---|---|
| DE | 29 38 844 A1 | 4/1981 |
| EP | 0 756 169 A2 | 1/1997 |
| WO | WO-01/69211 A1 | 9/2001 |

OTHER PUBLICATIONS

Baszkin, Adam; Norde, Willem; eds., "Physical Chemistry of Biological Interfaces", Marcel Dekker, Inc., New York, 2000, pp. 716–747.

(Continued)

*Primary Examiner*—Constantine Hannaher
(74) *Attorney, Agent, or Firm*—Connolly Bove Lodge & Hutz LLP; Larry J. Hume

(57) ABSTRACT

An apparatus and method capable of providing spatially multiplexed IR spectral information simultaneously in real-time for multiple samples or multiple spatial areas of one sample using IR absorption phenomena requires no moving parts or Fourier Transform during operation, and self-compensates for background spectra and degradation of component performance over time. IR spectral information and chemical analysis of the samples is determined by using one or more IR sources, sampling accessories for positioning the samples, optically dispersive elements, a focal plane array (FPA) arranged to detect the dispersed light beams, and a processor and display to control the FPA, and display an IR spectrograph. Fiber-optic coupling can be used to allow remote sensing. Portability, reliability, and ruggedness is enhanced due to the no-moving part construction. Applications include determining time-resolved orientation and characteristics of materials, including polymer monolayers. Orthogonal polarizers may be used to determine certain material characteristics.

87 Claims, 14 Drawing Sheets

OTHER PUBLICATIONS

D.L. Elmore, Mei–Wei Tsao, S. Frisk, D.B. Chase, J.F. Rabolt, Design and Performance of a Planar Array Infrared Spectrograph that Operates in the 3400 to 2000 cm–1 Region, Applied Spectroscopy, vol. 56, No. 2, 2002 pp 145–149.

R.G. Snyder, S.L. Hsu, and S. Krimm, Vibrational Spectra in the C–H Stretching Region and the Structure of the Polymethylene Chain, Spectrochimica Acta.vol. 34A, pp. 395–406, 1978.

CVI Product Template 5 for SM301 PbS Array Spectrometer, www.ovilaser.com/spectral/am301–929.asp?pcid=349 (downloaded and printed from WWW on Sep. 24, 2001).

M. Stetzie, J. Tuchtenhagen, J.F. Rabolt, Novel All–Fibre Optic Fourier Transform Spectrometer with Thermally Scanned Interferometer, Microchim, Acta [Suppl.] vol. 14, pp. 785–787, 1997.

Yamamoto, Kiyoshi; Ishida, Hatsuo; Interpretation of Reflection and Transmission Spectra for This Films: Reflection, Applied Spectroscopy, vol. 48, No. 7, 1994, p. 775–787.

Yamamoto, Kiyoshi; Ishida, Hatsuo: Optical theory applied to infrared spectroscopy, Vibrational Spectroscopy, 8 (1994), p. 1–38.

Gericke, Arne; Michailov, Alecander V; Huhnerfuss, Heinrich: Polarized external infrared reflection–absorption spectrometry at the air/water interface: comparison of experimental and theoretical results for different angles of Incidence, Vibrational Spectroscopy, 4 (1993), p. 335–348.

Mendelsohn, Richard; Brauner, Joseph W.; Garicke, Arne: External Infrared reflection absorption spectrometry of monolayer films at the air–water interface, Annu.Rec. Phys Chem 1995, 46, p. 305–333.

Grandbois, Michel; Dasbat, Bernard; Salesse, Christian: Monitoring of phospholipids monolayer hydrolysis by phospholipase A2 by use of polarization–modulation Fourier transform infrared spectroscopy, Biophysical Chemistry, 88 (2000), p. 127–135.

Grandbois, Michel; Desbat, Bernard; Blaudez, Daniel; Salesse, Christian: Polarization–Modulated Infrared Reflection Absorption Spectroscopy Measurement of Phospholipid Monolayer Hydrolysis by Phospholipase C, Langmuir, vol. 15. No. 19, 1999, p. 6594–6597.

Flach, Carol R.; Brauner, Joseph W.; Mendelsohn, Richard: Calcium Ion Interactions with Insoluble Phospholipid Monolayer Films at the A/W Interface, External Reflection-Absorption IR Studies, Biophysical Journal, vol. 65, Nov. 1993, p. 1994–2001.

Mitchell, Melody L.: Diuhy, Richard A.: In Situ FT–IR Investigation of Phospholipid Monolayer Phase Transitions at the Air–Water Interface, Journal of the American Chemical Society, 1988, 110, p. 712–718.

Diuhy, Richard A.; Reilly, Kim E.; Hunt, Rodney D.; Mitchell, Melody L.; Mautone, Alan J.; Mendelsohn, Richard: Infrared spectroscopic investigation of pulmonary surfactant Surface film transitions at the air–water Interface and bulk phase thermotropism, Biophysical Journal, vol. 56, Dec. 1989, p. 1179–1181.

Diuhy, Richard A: Quantitative External Reflection Infrared Spectroscopic Analysis of Insoluble Monolayers Spread at the Air–Water Infrared, The Journal of Physical Chemistry, vol. 90, No. 7, 1986, p 1379–1379.

Rabolt, J.F.; Burns, F.C.; Schlotter, N.W.; Swalen, J.D.; Molecular orientation in this monolayer films by infrared spectroscopy, Journal of Electron Spectroscopy and Related Phenomena, 30 (1983) p. 29–34.

Flach, Carol R.; Gericke, Arne; Mendelsohn, Richard: Quantitative Determination of Molecular Chain Tilt Angles in Monolayer Fims at the Air/Water Interface: Infrared Reflection/Absorption Spectroscopy of Bahanic Acid Methyl Ester, J. Phys. Chem. B., vol. 101, No. 1, 1997, p. 58–65.

Hunt, Rodney D.; Mitchell, Melody L.; Diuhy, Richard A.: The Interfacial Structure of Phospholipid Monolayer Films: and Infrared Reflectance Study, Journal of Molecular Structure, 214 (1989), p. 93–109.

Gericke, Arne; Mendelsohn, Richard: Partial Chain Deuteration as an IRRAS Probe of Conformational Order of Different Regions in Hexadacanoic Acid Monolayers at the Air/Water Interface, Langmuir, 1996, 12, p. 758–762.

Gericke, Arne; Flach, Carol R.; Mendelsohn, Richard: Structure and Orientation of Lung Surfactant SP–C and L–a–Dipalmitoylphosphatidylcholine in Aqueous Monolayers, Biophysical Journal, vol. 73, Jul. 1997, p. 492–499.

Knobler, Charles M.; Desai, Rashmi C.; Phase Transistions in Monolayers, Amu. Rec. Phys. Chem. 1992, 43, p. 208–236.

Blaudez, Daniel; Buffeteau, Thierry: Desbat, Bernard; Turiet, Jean Marie: Infrared and Ramam spectroscopies of monolayers at the air–water interface, Colloid & Interface Science, 4 (1999), p. 265–272.

Flach, Carol R.; Gericke, Arne; Mendelsohn, Richard: Quantitative Determination of Molecular Chain Tilt Angles in Monolayer Films at the Air/Water Interfaces: Infrared Reflection/Absorption Spectroscopy of Bahemic Acid Methyl Ester, J. Phys. Chem. B, 1997, 101, p. 58–65.

Buffeteau, T.; Blaudez, D.; Pere, E.; Desbat, B.; Optical Constant Determination in the Infrared of Unlaxially Oriented Monolayers from Transmittance and Reflectance Measurements, J. Phys. Chem B., 1999, 103, p. 5020–5027.

Buffeteau, T.; Le Calvez, E.; Castano, S.; Desbat, B.; Blaudez, D.; Dufouroq, J.: Anisotropic Optical Constants of a–Helix and B–Sheet Secondary Structures in the Infrared, American Chemical Society, p. 1–6 Washington DC Feb. 2000.

Dicko, Awa; Bourque, Helene; Pezoiet, Michel: Study by infrared spectroscopy of the conformation of dipalmitoylphosphatidylglycerol monolayers at the air–water interface and transferred on solid substrates, Chemistry and Physics of Lipids, 96 (1998), p. 125–139.

Flach, Carol R.; Gericke, Arne; Keough, Kevin M.W.; Mendelsohn, Richard: Palmitoylation of lung surfactant protein SP–C alters surface thermodynamics, but not protein secondary structure or orientation in 1, 2–dipalmitoylphosphatidylcholine Langmuir films, Biochimica et Biophysica Acta 1415 (1999), p. 11–20.

Flach, Carol R.; Xu, Zhi; Xiachong, Bl; Brauner, Joseph W.; Mendelsohn, Richard: Improved IRRAS Apparatus for Studies of Aqueous Monolayer Films: Determination of the Orientation of Each Chain in a Fatty–Acid Homogeneous Ceramide 2, Applied Spectroscopy, vol. 55, No. 8, 2001, p. 1060–1068.

Blaudez, D.; Boucher, F.; Buffeteau, T.; Desbat, B.; Grandbois, M.; Salesse, C.: Anisotropic Optical Constants of Bacteriorhodopain in the Mid–Infrared: Consequence on the Determination of a–Helix Orientation, Applied Spectroscopy, vol. 53, No. 10, 1999, p. 1299–1304.

Sahai, H.; Umemure, J.; Molecular Orientation in Langmuir Films of 12–Hydroxystearic Acid Studied by Infrared External–Reflection Spectroscopy, Langmuir, 1998, 14, p. 6249–6255.

S.M. Alawl, T. Krug, H.H.Richardson; Characterization and Application to an Infrared Linear Array Spectrometer for Time–resolved infrared Spectroscopy, Applied Spectroscopy, vol. 47, No. 10, 1993, pp. 1626–1630.

H.H. Richardson, V.W. Pabst, J.A. Butcher, Jr., A Novel Infrared Spectrometer Using a Linear ARray Detector, Applied Spectroscopy, vol. 44, No. 5, 1990, pp. 822–825.

J. Zhao, R.L. McCreery, Multichannel Gourier Transform Raman Spectroscopy: Combining the Advantages of CCDs with Interfereometry, Applied Spectroscopy, vol. 50, No. 9, 1996, pp. 1209–1214.

P. Hamm, B. Wiemann, M. Zurek, W. Zinth, Highly Sensitive Multichannel Spectrometer for Subpicosecond Spectroscopy in the Mid Infrared, Institut fur Mediznische Optik, Optics Letters, vol. 19., No. 20, pp. 1042–1044, Apr. 1994.

* cited by examiner

FIG. 1 – FOURIER TRANSFORM IR (FTIR) MICHELSON INTERFEROMETER (BACKGROUND ART)

INTERFEROMETRIC SPECTROPSCOPY USING NO MOVING PARTS
(BACKGROUND ART)

NON-INTERFEROMETRIC IR SPECTROSCOPY USING NO MOVING PARTS

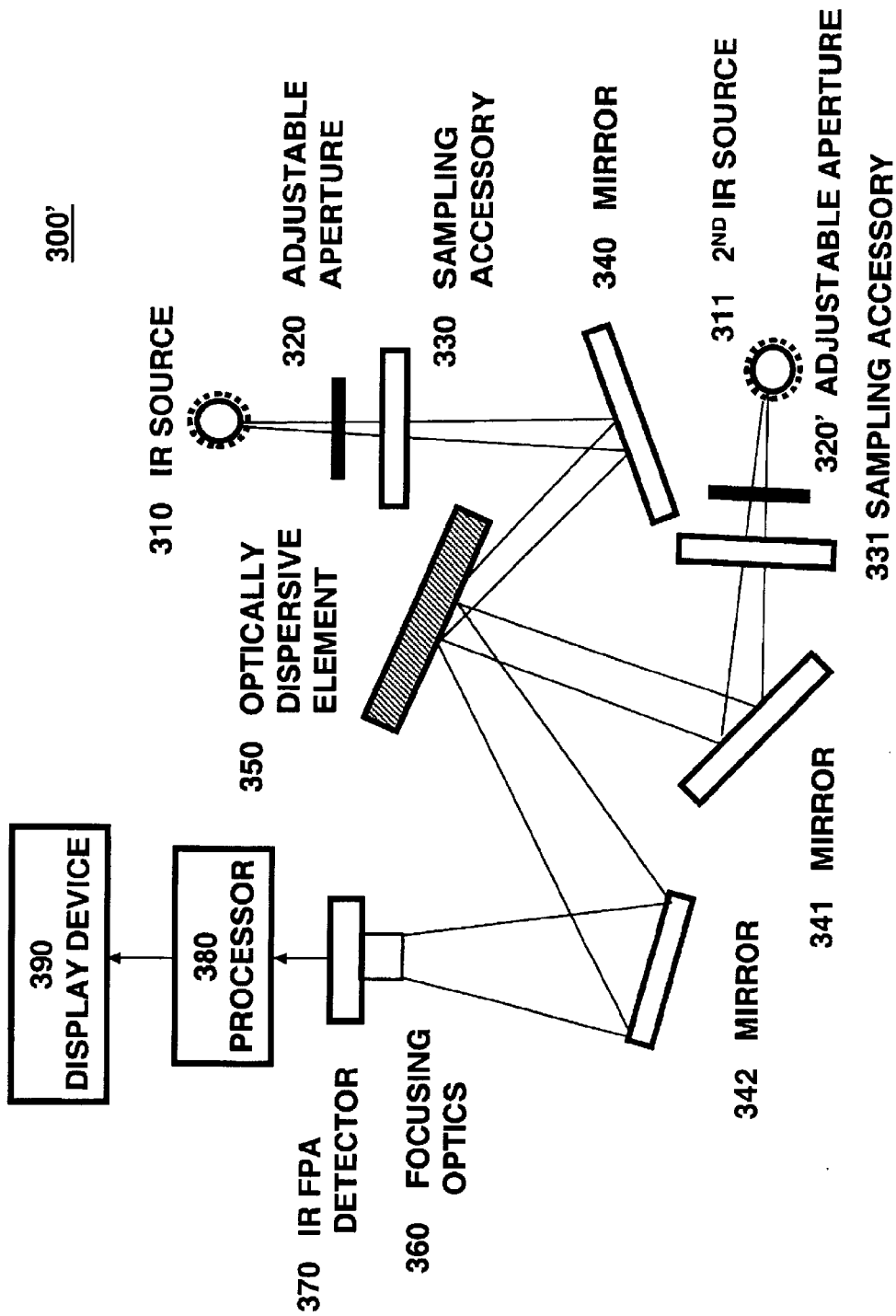

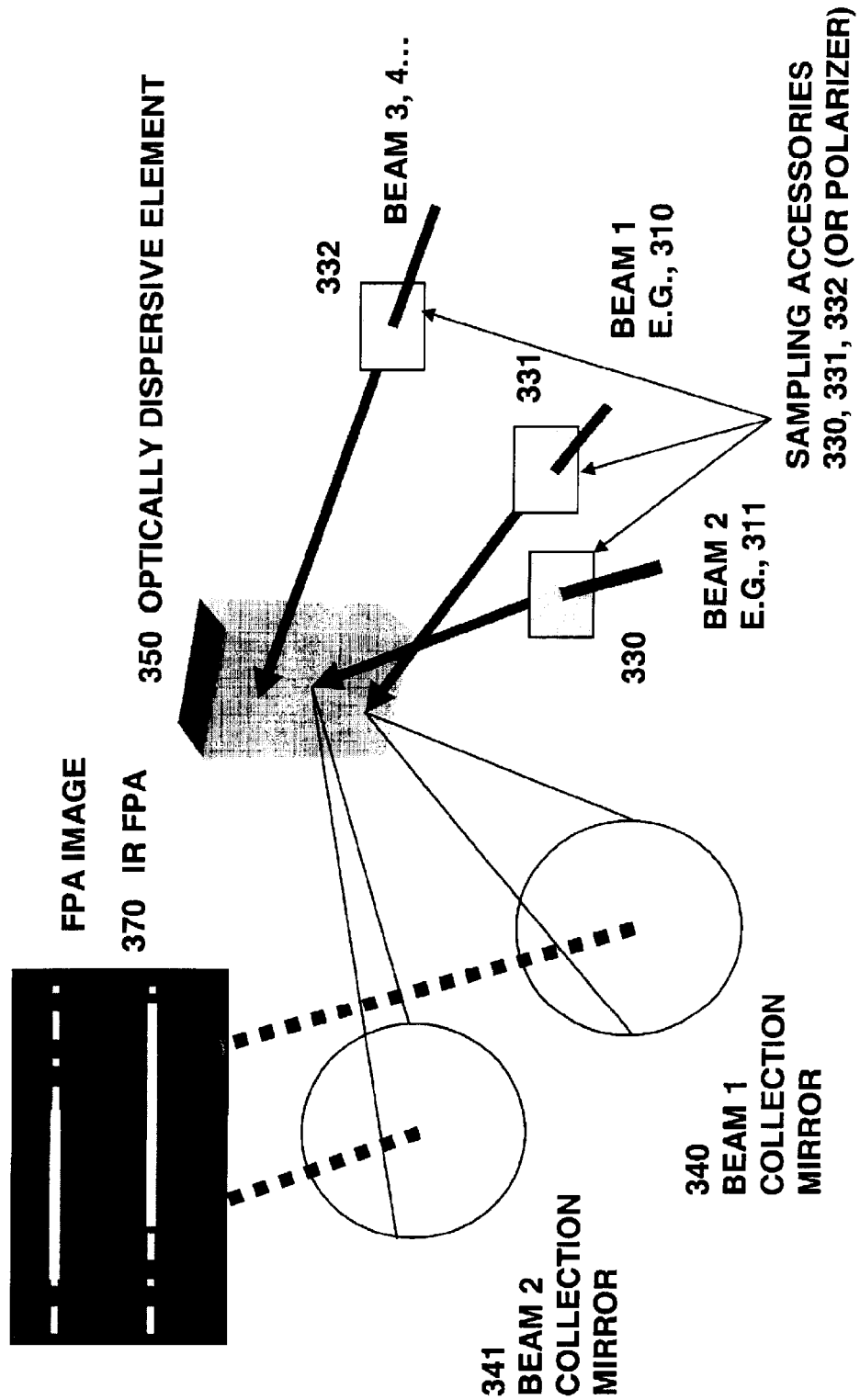

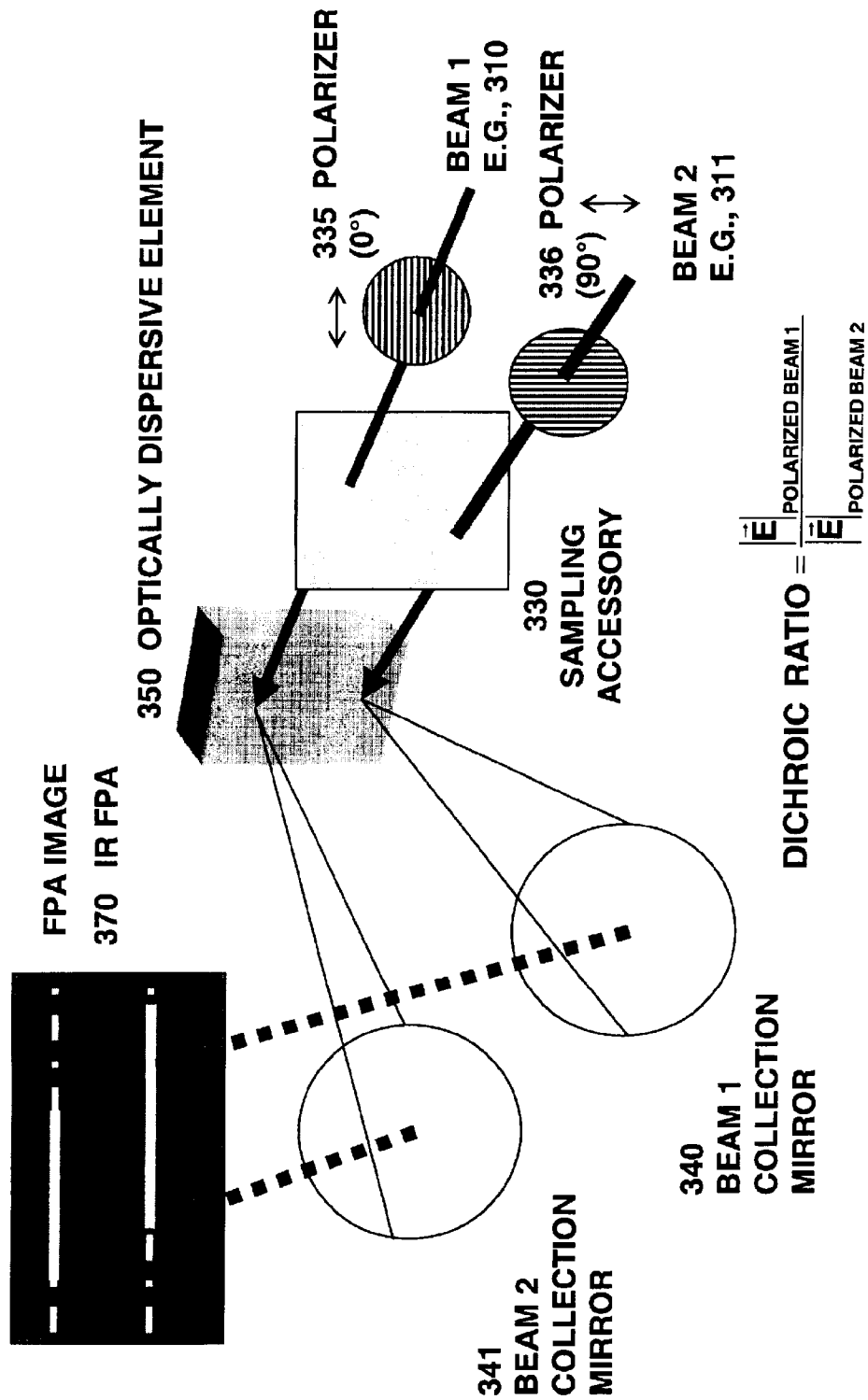

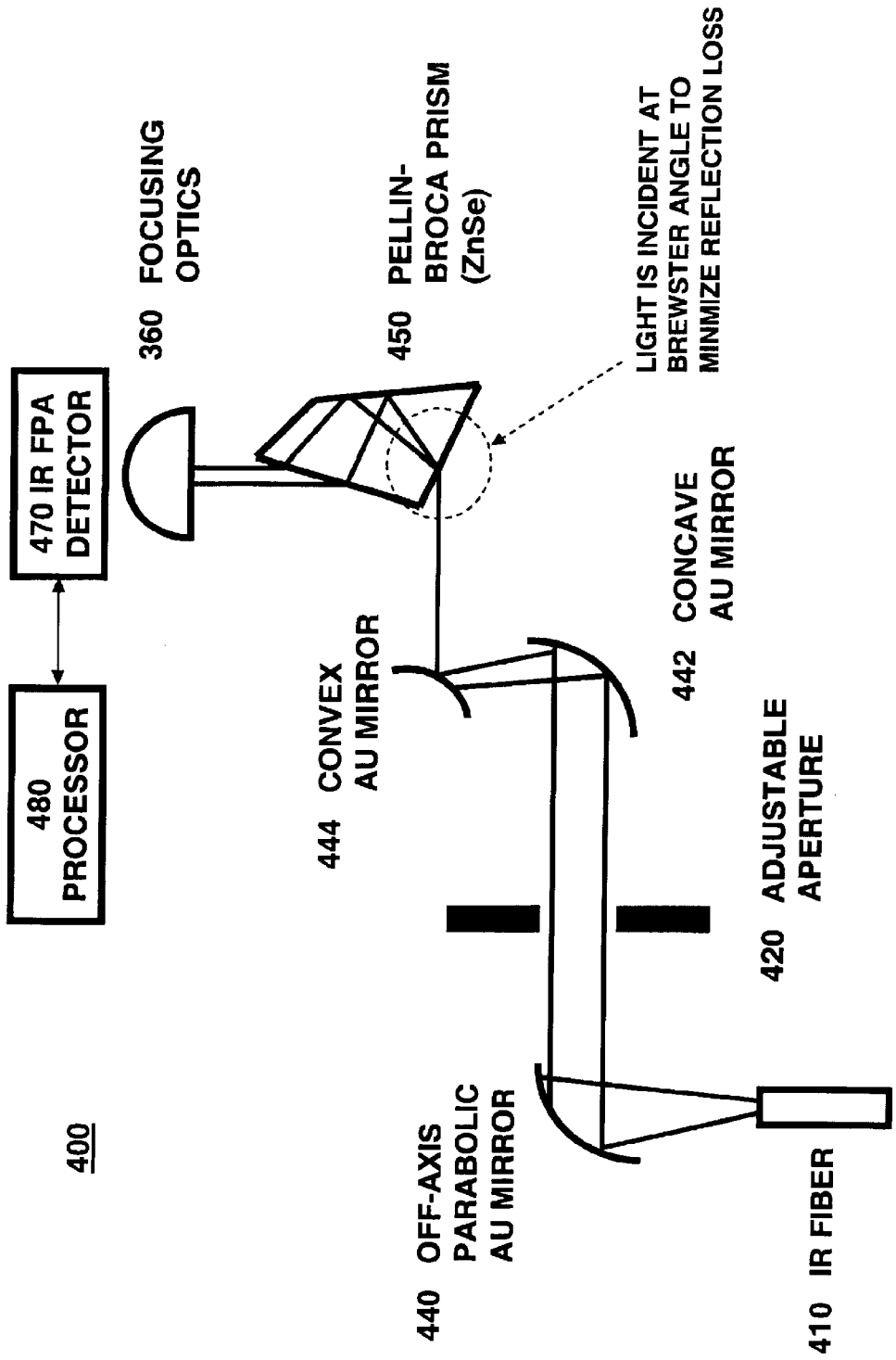
FIG. 4 – PELLIN-BROCA PRISM IMPLEMENTATION

ZnSe REFRACTIVE INDEX DISPERSION AND OPTICAL REFRACTION
PELLIN-BROCA PRISM IMPLEMENTATION

CONFIGURATION FOR REAL-TIME BACKGROUND CORRECTION

MEASURING MULTIPLE ANGLES OF INCIDENCE

STRATIFIED THREE-PHASE SYSTEM

REFLECTION/REFRACTION MEASUREMENT FOR DETERMINING OPTICAL CONSTANTS OF A THIN FILM

POLARIZATION MODULATION INFRARED REFLECTANCE-ABSORBANCE SPECTROSCOPY (CONVENTIONAL PM-IRRAS USED WITH FTIR)

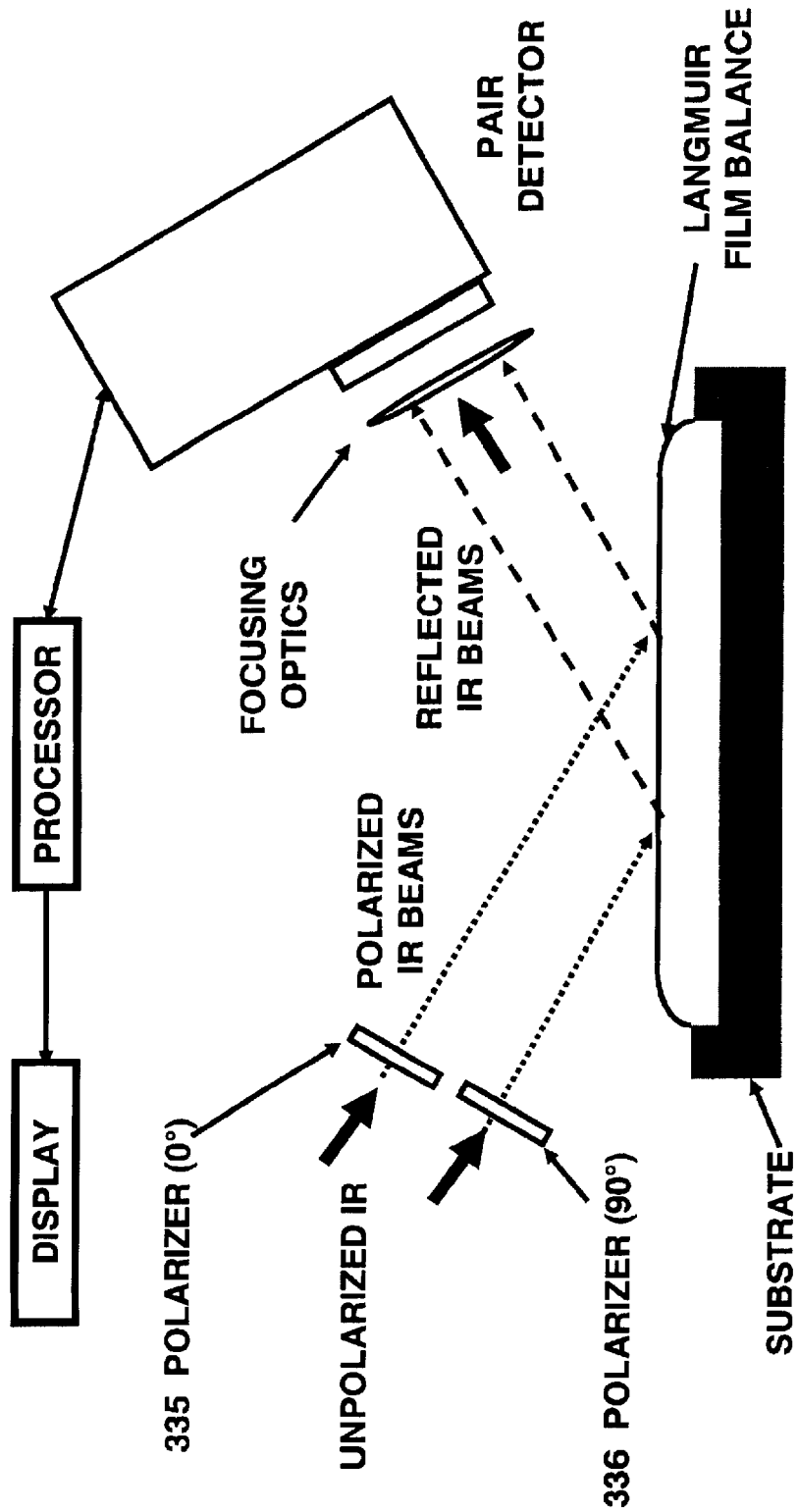

SIMULTANEOUS MULTI-BEAM PLANAR ARRAY IR (PAIR) SPECTROSCOPY

CROSS REFERENCE TO RELATED APPLICATIONS

This Application is a Continuation of International Patent Application PCT/US02/08346 filed on Mar. 19, 2002, the entire contents of which are incorporated herein by reference. International Patent Application PCT/US02/08346 is a Continuation-in-part of U.S. patent application Ser. No. 09/984,137 filed on Oct. 29, 2001, now U.S. Pat. No. 6,784,428, and Ser. No. 09/984,137 is a Continuation of International Patent Application PCT/US01/30724 filed on Oct. 1, 2001, the entire contents of each of which are also incorporated herein by reference.

GOVERNMENT LICENSE RIGHTS

The United States Government may have certain rights in this invention as provided for by National Science Foundation (NSF) Grant No. 0076017, and Department of Energy Grant No. DE-FG02-99-ER45794.

BACKGROUND

This disclosure relates generally to an apparatus and method for simultaneously determining an IR spectrum of multiple sample materials. More particularly, various embodiments of the disclosure relates to spatial multiplexing of spectroscopically determined IR spectra of multiple samples using an apparatus and method that operate in real-time with simultaneous background compensation, and which do not require the use of any moving parts. Still further, the apparatus and method of the disclosure do not require extensive mathematical transformation of the detected spectral information to analyze the composition of the sample material.

This disclosure has industrial applicability to, for example, a real-time method to monitor manufacturing processes. Such processes include, but are not limited to measurement of thickness, chemical structure, and orientation of coatings on surfaces (solid, liquid, chemically bound, physically adsorbed). These measurements include, but are not limited to those made on biological materials, polymers, superconductors, semiconductors, metals, dielectrics, and minerals. Further applicability is found to a real-time apparatus and method to measure and detect a chemical species present in a chemical reaction involving various processing of materials in any of a gaseous, liquid, or solid state. In addition, the apparatus and method of this disclosure provides for self-compensation, to account for sensor or optical path changes over time, or changes in environmental conditions, which may affect the measurements obtained.

As industry continues on its path of cost reductions in core technologies, more emphasis will be placed on the optimization of processes and performance. This retrenchment will necessitate the development and introduction of a whole new class of sophisticated instrumentation that is portable, rugged, reliable, and capable of operation over long periods of time in an aggressive industrial or other non-laboratory environment.

Spectrometric techniques are often used in analysis of materials. Classically, spectroscopy is the measurement of the selective absorption, emission, or scattering of light (energy) of specific colors by matter. Visible white light can be separated into its component colors, or spectrum, by a prism, for example. The principal purpose of a spectroscopic measurement is usually to identify the chemical composition of an unknown material, or to elucidate details of the structure, motion, or environmental characteristics (e.g., internal temperature, pressure, magnetic field strength, etc.) of a "known" material or object. Spectroscopy's widespread technical importance to many areas of science and industry can be traced back to nineteenth-century successes, such as characterizing natural and synthetic dyes, and determining the elemental compositions of stars.

Modern applications of spectroscopy have generalized the meaning of "light" to include the entire range or spectrum of electromagnetic radiation, which extends from gamma-and x-rays, through ultraviolet, visible, and infrared light, to microwaves and radio waves. All these various forms (or wavelength ranges) of electromagnetic radiation have their own characteristic methods of measurement. These different methods give rise to various types of spectroscopic apparatus and techniques that are outwardly very different from each other, and which often rely upon difference physical phenomena to make measurements of material characteristics. Further, the various experts and other researchers in these diverse fields, more often than not, do not cross the technical boundaries between these areas of specialization, as different and somewhat compartmentalized knowledge bases and "rules of thumb" are used.

The use of infrared (IR) is one of numerous spectroscopic techniques for analyzing the chemistry of materials. In all cases, spectroscopic analysis implies a measurement of a very specific wavelength of light energy, either in terms of the amount absorbed or reflected by the sample in question, or the amount emitted from the sample when suitably energized.

In the case of IR, an absorption form of spectrometric analysis is relied upon. IR radiation does not have enough energy to induce transitions between different electronic states, i.e., between molecular orbitals, as seen with ultraviolet (UV), for example. Unlike atomic absorption, IR spectroscopy examines vibrational transitions within a single electronic state of a molecule, and is not concerned with specific atomic elements, such as Pb, Cu, etc. Such vibrations fall into one of three main categories, i.e., stretching, which results from a change in inter-atomic distance along the bond axis; bending, which results from a change in the angle between two bonds; and torsional coupling, which relates to a change in angle and separation distance between two groups of atoms. Almost all materials absorb IR radiation, except homonuclear diatomic molecules, e.g., $O_2$, $H_2$, $N_2$, $Cl_2$, $F_2$, or noble gases.

IR typically covers the range of the electromagnetic spectrum between 0.78 and 1000 $\mu$m. Within the context of IR spectroscopy, temporal frequencies are measured in "wavenumbers" (in units of $cm^{-1}$), which are calculated by taking the reciprocal of the wavelength (in centimeters) of the radiation. Although not precisely defined, the IR range is sometimes further delineated by three regions having the wavelength and corresponding wavenumber ranges indicated:

"near-IR": 0.78–2.5 $\mu$m 12800–4000 $cm^{-1}$;
"mid-IR" 2.5–50 $\mu$m 4000–200 $cm^{-1}$; and
"far-IR" 50–1000 $\mu$m 200–10 $cm^{-1}$ For a molecule to absorb IR, the vibrations or rotations within the molecule must cause a net change in the dipole moment of the molecule. The alternating electric field of the incident IR radiation interacts with fluctuations in the dipole moment of the molecule and, if the frequency of the radiation matches the vibrational frequency of the molecule, then radiation will be absorbed, causing a reduction in the IR band intensity due to the molecular vibration.

An electronic state of a molecular functional group may have many associated vibrational states, each at a different energy level. Consequently, IR spectroscopy is concerned with the groupings of atoms in specific chemical combinations to form what are known as "functional groups", or molecular species. These various functional groups help to determine a material's properties or expected behavior by the absorption characteristics of associated types of chemical bonds. These chemical bonds undergo a change in dipole moment during a vibration. Examples of such functional groups and their respective energy bands include, for example, hydroxyl (O—H) (3610–3640 $cm^{-1}$), amines (N—H) (3300–3500 $cm^{-1}$), aromatic rings (C—H) (3000–3100 $cm^{-1}$), alkenes (C—H) (3020–3080 $cm^{-1}$), alkanes (C—H) (2850–2960 $cm^{-1}$), nitriles (C≡N) (2210–2260 $cm^{-1}$), carbonyl (C═O) (1650–1750 $cm^{-1}$), or amines (C—N) (1180–1360 $cm^{-1}$). The IR absorption bands associated with each of these functional groups act as a type of "fingerprint" which is very useful in composition analysis, particularly for identification of organic and organometallic molecules.

By knowing which wavelengths are absorbed by each functional group of interest, an appropriate wavelength can be directed at the sample being analyzed, and then the amount of energy absorbed by the sample can be measured. The intensity of the absorption is related to the concentration of the component. The more energy that is absorbed, the more of that particular functional group exists in the sample. Results can therefore be numerically quantified. Further, the absence of an absorption band in a sample can often provide equally useful information.

Intensity and frequency of sample absorption are depicted in a two-dimensional plot called a spectrum. Intensity is generally reported in terms of absorbance, the amount of light absorbed by a sample, or percent transmittance, the amount of light that passes through it. In IR spectroscopy, frequency is usually reported in terms of wavenumbers, as defined above.

Infrared spectrometers may be built using a light source (e.g., the sun), a wavelength discriminating unit or optically dispersive element such as a prism, for example, and a detector sensitive to IR. By scanning the optically dispersive element, spectral information may be obtained at different wavelengths, by using either a reflection mode, i.e., reflection of the light source off the sample, or a transmission mode, i.e., transmitting a portion of the light source through the sample. However, one drawback to this approach is the moving parts associated with the required scanning operation. Such moving parts inherently limit the ruggedness and portability, for example, of such a device.

More recently, a Michelson interferometer has been used to generate a so-called interferogram in the IR spectrum, which later is subjected to Fourier transform processing such as a fast Fourier transform (FFT) to yield the final spectrum. In the IR range, such spectrometers are called FTIR interferometers, and the first commercially available appeared in the mid 1960's. A representation of an FTIR interferometer is provided in FIG. 1.

The key components of FTIR interferometer 100 are IR source 110, interferometer (130, 140, 150), and IR detector 160. FTIR interferometer 100 provides a means for the spectrometer to measure all optical frequencies transmitted through sample 120 simultaneously, modulating the intensity of individual frequencies of radiation before detector 160 picks up the signal. Typically, moving mirror arrangement 150 is used to obtain a path length difference between two (initially) identical beams of light. After traveling a different distance than a reference beam, the second beam and the reference beam are recombined, and an interference pattern results. IR detector 160 is used to detect this interference pattern.

The detected interference pattern, or interferogram, is a plot of intensity versus mirror position. The interferogram is a summation of all the wavelengths emitted by the sample and, for all practical purposes, the interferogram cannot be interpreted in its original form. Using the mathematical process of Fourier Transform (FT), a computer or dedicated processor converts the interferogram into a spectrum that is characteristic of the light either absorbed or transmitted through sample 120.

The development of FT spectroscopy has proven to be one of the most important advances in modern instrumentation development in the 20th Century. Optical spectroscopy utilizing the interference of light has made fast, sensitive detection of molecular vibration/rotation possible due to the large throughput and multiplex advantages provided by FT instrumentation. In Nuclear Magnetic Resonance (NMR) and mass spectroscopy where high-resolution spectra are required, FT instrumentation has also prevailed as the state of the art.

The same technological innovations that have made FT instruments those of choice for a generation of spectroscopists, however, have also made them extremely sensitive to their operating environment. For these reasons, FT interferometers are mostly limited to laboratory conditions which require the use of an optical bench to prevent vibration, and which also require stringent environmental controls to control temperature variations that adversely affect the interferogram by thermally inducing path length differences. While this type of scanning approach has proven to be workable, the signal-to-noise-ratios (SNR) obtainable in some situations often require substantial signal averaging of multiple interferograms, thus making FTIR systems inherently slower than desired under some circumstances, with reduced speed and potentially lower reliability resulting from the numerous moving parts of these systems.

In spectroscopy, resolution is a measure of the ability to resolve or differentiate two peaks in the spectrum, where high resolution corresponds to a small wavenumber difference between the peak positions, and low resolution is associated with a larger wavenumber difference between the peak positions. Fourier Transform interferometers are capable of extremely high resolution, on the order of $\frac{1}{1000}^{th}$ $cm^{-1}$, depending on the amount of possible movement of the mirror, or the path length difference that can be generated by the particular apparatus. "Low" resolution is generally considered to be in the range of 16–32 $cm^{-1}$, although no bright-line demarcation between "low" and "high" resolution exists, as resolution is chosen based on the required measurement and specific application. For typical chemical analysis and identification associated with FTIR, "high" resolution of 8 $cm^{-1}$ or better is common. Otherwise, chemical information is lost if the resolution is too low, as adjacent peaks identified with a particular chemical bond or vibration state may be "smeared" together and rendered indiscernible if a lower resolution is used.

The need for thermal stability, mechanical vibration isolation, and stringent optical alignment has put severe constraints on where and how FT instruments can be used and, in particular, has limited the portability of such instruments. If discussion is limited to FTIR interferometers, then an examination of the specific technology used in currently available instruments reveals where some of the shortcomings can be found. Table 1 compares the four most commonly used techniques for the operation of an optical interferometer, and their limitations.

TABLE 1

Common FTIR Interferometer Designs and their Limitations

| Operating Technologies | Limitations |
| --- | --- |
| Air-Bearings | Requires stable supply of clean, dry air and a tightly leveled travel plane for the moving mirror. Low tolerance for vibration. |
| Magnetic Coils | Requires highly regulated power supplies. Low tolerance for vibration. |
| Piezo Stacks | Limited travel range. High voltage power supplies needed to operate the piezo elements. |
| Mechanical/Piezo Hybrid | Requires large mechanical structures and complicated feedback system for piezo element operation. |

FTIR has been applied to a variety of studies in industry, government, and academic laboratories, and has resulted in a major improvement upon conventional methods of performing analysis on a variety of samples. However, it has become clear that the moving mirror mechanism in a traditional interferometer has limited the design and construction of a more compact and portable FTIR. One potential solution attempted by Stelzle, Tuchtenhagen, and Rabolt ("Novel All-fibre-optic Fourier-transform Spectrometer with Thermally Scanned Interferometer"), was to construct an all-fiber-optic FT Spectrometer, which had no moving parts, and which was used to perform infrared spectroscopy.

In this feasibility study, an attempt was made to build an interferometer in the near-IR (10000-5000 $cm^{-1}$) range using fiber optics. Two carefully measured and cleaved optical fibers were used as the two light channels, or optical paths, with one fiber kept at ambient temperature while the other fiber was heated/cooled repeatedly. The resulting optical path difference (OPD) between the two fiber channels due to changes in both the length and the refractive index of the heated/cooled fiber caused interference in the combined channel. The heating/cooling cycle was used to generate an OPD of 3 cm, thus producing an interferogram with the power spectrum calculated accordingly.

However, the interference of two light beams in the optical fibers under different thermal and mechanical conditions turned out to be very complex. In contrast to the traditional Michelson interferometer, whose only source of optical path length difference comes from the geometric path length resulting from the moving mirror, a fiber-optic interferometer responds to any mechanical or thermal changes of the operating environment, which causes a scrambling or loss of the phase information necessary for interference to occur. It was concluded that although the fiber optics concept is a good one, a more prudent plan for a no-moving parts IR instrument had to be developed.

In surveying the literature, it became apparent that, without regard to the band of interest, e.g., visible, near-IR, or IR, other approaches to the construction of an FT interferometer with no-moving parts had also been attempted, as depicted in FIG. 2. Such approaches used either a linear array detector or a focal plane array (FPA) to collect interferograms. These designs involved the projection of the center portion of the interferogram onto the detector, and then used the "imaged" interferograms to calculate the power spectra after Fourier Transform processing. One difficulty of these conventional techniques is that the array detector size, its dynamic range, and the limited range of spectral response available limited the range of the interferograms that could be captured by the array detector.

In addition, even without moving parts, these approaches still rely upon calculation-intensive Fourier Transform processing to derive the power spectrum. Hence, there is still a need for a rugged, non-interferometric, no-moving part spectrometer in the mid-IR range.

Aside from, and even prior to Fourier Transform spectroscopy, spectroscopy based on dispersion provided a possible implementation. In this approach, an optically dispersive element, such as a prism or diffraction grating, is used to separate the spectral frequencies present in the incident light radiation. The dispersive element was then rotated, in order to allow the various wavelengths present in the incident light to be detected.

IR spectroscopy based on dispersion became obsolete in most analytical applications in the late 1960's due to its slow scan rate and lower sensitivity. It is well known that the scanning mechanism in a dispersive spectrometer, e.g., a moving prism, intrinsically limits both its ruggedness and optical throughput. The need for scanning comes from the fact that point detection of photons was the only available method at that time, and this was especially true in the IR range of the spectrum. Today, however, array detectors in the visible and near-IR range are widely available for area detection of photons. Charge-coupled-devices (CCD) capable of >80% quantum efficiency (QE) in the visible range have been made and utilized in many applications, such as the visible/near-IR camera aboard the Hubble Space telescope. As a result of this progress, CCD-based high performance spectrograph systems in the visible and near-infrared range can now be purchased through commercial suppliers. These systems provide alternatives to traditional FT interferometers.

However, the range of scientific problems which could now benefit from IR investigations has increased significantly, and applications involving samples which may change their position in the beam (e.g., vibrate or oscillate) while the spectrum is being recorded can not be routinely addressed using conventional FTIR instruments. The scanning architecture of FTIR instruments and the resulting modulation of the different optical frequency components can become modified further by a sample whose position fluctuates, and this can render the spectral information useless.

For example, few techniques exist which can provide insitu structural information about Langmuir films. Infrared reflectance-absorbance spectroscopy (IRRAS) is a non-destructive technique that provides direct structural information about either the expanded or condensed phase of a Langmuir monolayer. The technique can also provide information about both the hydrocarbon tails and the head groups independently by monitoring vibrational modes with frequencies in the 4000 to 400 $cm^{-1}$ region. Because polarized infrared spectroscopic measurements are sensitive to the orientation of transition-dipole moments, IR-RAS can be used to determine the orientation of different subcomponents of an amphiphilic molecule.

Since, in order to fabricate Langmuir-Blodgett (LB) films, Langmuir monolayers of these amphiphilic polymers must be first formed on a water surface, where their thermodynamic state of order is known to have a dramatic effect on the structure of the transferred LB films. Hence, it becomes critically important to understand the structure of the monolayer in situ on the water surface under conditions for which the thermodynamics are well understood. One of these conditions is the continuous compression of the Langmuir monolayer film since, in general, the most accurate and reproducible thermodynamic measurements have been obtained during this process. However, to date, pressure-dependent IRRAS spectra have been collected exclusively in a "step-wise" manner, i.e., no IRRAS spectra have been reported that correspond to a Langmuir mono-layer undergoing a continuous compression.

While IRRAS using conventional FTIR spectroscopy offers a variety of instrumental advantages for investigating thin films compared to standard transmission measurements, the technique does suffer from several inherent limitations. The inherently weak monolayer absorbance bands result in a relatively poor signal-to-noise (S/N) spectrum and, since environmental fluctuations are difficult to minimize, spectral compensation for the water vapor that is present above the Langmuir trough remains a challenge.

Over the last decade the S/N observed in IRRAS experiments on dielectric substrates has gradually improved due to advances in the instrumentation and in the optical interface. There are a variety of ways to minimize the problem of water vapor compensation, including strict humidity control and a shuttle transport system that allows a sample trough to be repeatedly replaced with a reference trough allowing both a sample and reference spectrum to be recorded.

Another way to minimize the problem of water vapor compensation includes the application of polarization modulation infrared reflectance-absorbance spectroscopy (PM-IRRAS). In PM-IRRAS, the polarization of the incident beam undergoes a fast modulation between two orthogonal directions via a photoelastic modulator. The detected signal passes through a two-channel electronic system and is mathematically processed to give a differential reflectivity spectrum. In theory, because of the fast polarization modulation, the PM-IRRAS signal is devoid of all polarization-independent signals such as strong water vapor absorptions, instrumental drifts and fluctuations.

Despite the previously mentioned limitations, the IRRAS or PM-IRRAS technique has been used to investigate a variety of Langmuir monolayers, including studies of fatty acid, phospholipid and phospholipid-protein monolayers. The technique has been used to provide information on lipid conformation, molecular tilt angle, and the structure of head groups, as well as protein secondary structure and orientation. However, neither IRRAS nor PM-IRRAS (both of which utilize FTIR) have been able to provide in situ timeresolved measurements of Langmuir monolayers in the 1 ms to 1 s time regime, nor have any of the known techniques been able to simultaneously provide multiple independent measurements.

Hence, the need for a non-scanning instrument with convenient delivery and detection of IR radiation could never be stronger. For example, applications requiring on-line studies of micro mechanical deformation in polymer thin films during processing, in situ structural studies of aging in Light Emitting Diodes (LEDs), and the monitoring of in-organic (silicon, SiN, etc.) thin film growth on flexible polymer substrates would all benefit from an IR instrument with no moving parts, which as a consequence, will also be robust and portable. Such a portable instrument would facilitate materials research by providing a powerful new tool for thin film studies, especially those with fluctuating sampling geometries or in a remote sample location.

Further advantages for such a non-scanning, real-time instrument in the IR range could be found in environmental monitoring, including monitoring near military or civilian personnel during potential chemical or biological warfare attacks. The complex chemical compositions in such agents show strong IR absorbance, and thus could be readily identified.

In spite of the inroads made in spectroscopy by spectrographs in the visible and near-infrared range, primarily due to the progress in CCD detectors mentioned previously, FT instrumentation still remains dominant in spectroscopy in the mid to far-infrared range and, therefore, instruments in this range are still extremely limited by the operating environment of the interferometer.

Further, all spectral techniques require the collection of a reference spectrum for comparison with that obtained from the sample. In almost all cases, these two measurements are done in series, basically doubling the time of measurement. If this time is long, as in the case of obtaining spectra of thin films or of molecules in the gas phase, then variations in the instrument or sample conditions, for example, due to temperature or humidity fluctuations in the instrument or environment, can prevent compensation of the instrumental background.

Thus, making background and sample measurements in parallel removes or compensates for any instrumental fluctuations, reduces the total time of spectral collection, preserves sample integrity in case there is "aging" or degradation with time, and provides additional advantages in the portability of such an instrument since "realtime" background compensation in aggressive field or non-laboratory environments can be made.

What is needed, then, is a robust, compact, and portable instrument (with no moving parts) in the IR range to address specific applications where sample fluctuations cause significant deterioration of the signal-to-noise ratio in conventional FTIR spectra.

What is further needed is a portable and reliable IR spectroscope which allows multiple, simultaneous spectral measurements.

Still what is further needed is a real-time, sensitive and relatively high-resolution apparatus and method for IR spectroscopic materials analysis, which does not rely upon interferometric or a calculation-intensive Fourier Transform approach, and which is relatively insensitive to harsh environments, including high vibration and wide temperature variations, and which provides the ability to compensate for background spectral components and component degradation in real-time.

There is, therefore, also a need for an apparatus and device capable of collecting multiple independent spectra simultaneously with background environment compensation and compensation for the aging of components, including orthogonally polarized measurements, which allows time-resolved measurements on Langmuir monolayers, including time-resolved molecular orientation measurements.

BRIEF SUMMARY

Various embodiments of this disclosure solve many of the aforementioned problems of providing a robust, high-resolution and sensitive apparatus and method for determining background-compensated IR spectra of multiple samples, without the use of moving parts, or calculation-intensive Fourier Transform interferometric techniques.

The multi-beam planar array infrared (PAIR) spectrograph offers numerous advantages over conventional FT-IR interferometry for a variety of important materials characterization applications. Some of these include routine IR spectroscopy, time-resolved IR spectroscopy, timeresolved spectroscopic imaging, monolayer spectroscopy and on-line monitoring of processes in aggressive environments. The PAIR spectrograph may also be used to investigate fundamental dynamics associated with thick and thin polymer films undergoing an irreversible change.

An extension of the apparatus and method disclosed and claimed in International Application PCT/US01/30724 and U.S. application Ser. No. 09/984,137 to two or more background-ground compensated beam measurement is made possible, at least in part, by use of a focal plane array (FPA) detector having a relatively large area. For example, a 320×256 pixel Indium-Antimonide (InSb) FPA detector, or other suitable material, may be used in the construction of the PAIR spectrograph. Multiple beams from multiple samples or multiple spatial areas of one sample, may be dispersed by one or more prisms or gratings, and simultaneously focused on the detector.

At least one of these multiple samples could be a background reference sample, from which the spectrum of the background environment could be determined. This allows background compensated data from several samples to be collected simultaneously in real-time, or compensated data from several spatial locations in the same sample could be collected simultaneously. In addition, IR polarizers selective to certain electric field components of the IR beam can be inserted in the optical path, thus providing for simultaneous collection of IR dichroic data.

Multi-beam PAIR spectroscopy can be used for the "real-time" spatial mapping of films for quality control applications in a processing line. Compensation for environmental factors, e.g. spectral compensation for water vapor present in the optical path, or for the aging characteristics of the sensor can also be accomplished in real-time, with-out complicated calibration procedures. It can also be used for detection of chemical toxins and, if used in conjunction with an analyte or bio-specific reagent, it can be used to detect biological agents in the environment, e.g., virus or bacteria. Further, multiple beam PAIR using the apparatus and method of this disclosure can also be used to measure pollutants in water, dielectric film growth in semiconductors, and the development of orientation in a polymer film production line.

One aspect of this disclosure includes an apparatus for determining an IR spectrum of a plurality of sample materials using IR FPA technology to capture the IR spectral information for each of the samples, without utilizing a scanning mechanism, or any moving parts, and without the use of computation-intensive signal processing, e.g., Fourier Transform.

This aspect includes an apparatus for simultaneously spatially multiplexing IR spectral information for each of a plurality of samples, and includes at least one IR light source; at least one sample holder which positions the plurality of samples in an optical path; an optically dispersive element in the optical path, wherein an emission from the at least one IR light source interacts with each of the plurality of samples along the optical path to form a corresponding plurality of sample emissions, said plurality of sample emissions interacting with the optically dispersive element to form a corresponding plurality of dispersed sample light beams, each of said plurality of dispersed sample light beams corresponding to a respective one of the plurality of samples; and an IR FPA detector arranged in the optical path, said IR FPA detector having multiple pixels arranged in plural rows and columns, wherein the IR FPA detector detects the corresponding plurality of dispersed sample light beams and provides at least one output which represents the IR spectral information for each of the plurality of samples.

In another aspect of this disclosure, a real-time, noninterferometric apparatus using IR absorption phenomena and no moving parts during operation to simultaneously perform chemical analysis in a plurality of sample volumes includes a broadband light source; at least one sampling accessory for positioning the plurality of sample volumes so that at least a portion of light emitted from the broad-band light source interacts with each of the plurality of sample volumes; adjustable means for optically dispersing the at least a portion of light interacted with each of the plurality of sample volumes to obtain a plurality of corre-sponding dispersed sample beams; a two-dimensional IR detector array having a plurality of detector elements arranged in rows and columns, optical coupling means for coupling the plurality of corresponding dispersed sample beams onto the two-dimensional IR detector array; and processor means for controlling the two-dimensional IR detector array and providing non-interferometric chemical analysis of said plurality of samples based at least upon an IR absorption spectrum in one or more particular wavelength regions, wherein each of the plurality of corresponding dispersed sample beams are projected on multiple rows in a different area of the two-dimensional IR detector array, and corresponding column detector elements in each of the multiple rows are added together within each different area of the two-dimensional IR detector array to determine an intensity of an IR spectral component at a particular wavelength in real time, wherein a signal-to-noise-ratio of a signal representing the intensity of the IR spectral component at the particular wavelength is increased by adding the corresponding column detector elements in each of the multiple rows.

In a method relating to this aspect of the disclosure, chemical analysis of the plurality of samples is performed by determining an IR absorption spectrum of each of the plurality of samples. The method includes projecting at least a portion of an emission of the broadband light source onto the plurality of sample volumes; interacting the at least a portion of an emission of the broadband light source with the plurality of sample volumes; providing a corresponding plurality of sample emissions to an optically dispersive element; forming a plurality of corresponding dispersed sample beams; optically coupling the plurality of corresponding dispersed sample beams onto the two-dimensional IR detector array, wherein each of the plurality of corresponding dispersed sample beams are projected on multiple rows in a different area of the two-dimensional IR detector array; non-in-terferometrically processing, within each different area of the two-dimensional IR detector array, an output from each detector in a plurality of rows of detectors, wherein each column of detectors represents a particular wave-length within each different area; determining the IR absorption spectrum of each of the plurality of samples by evaluating a processed output from said each detector; and at least partially analyzing a chemical makeup of each of the plurality of samples by comparing the processed output to one or more reference standards.

In another aspect of this disclosure, a method of simultaneously determining an IR spectrum of a plurality of sample volumes using a non-interferometric apparatus capable of operating using no moving parts is disclosed. The method includes providing an IR source; positioning the plurality of sample volumes in an optical path; interacting at least a portion of an emission of the IR source with the plurality of sample volumes along the optical path to form a plurality of sample emissions; optically dispersing the plurality of sample emissions to form a corresponding plurality of dispersed sample beams; detecting each of the plurality of dispersed sample beams on spatially separated areas on a focal plane array having rows and columns of pixels thereon; and simultaneously and non-interferometrically determining the IR spectrum of each of the plurality of sample emissions by evaluating a combined output from each spatially separated area of the focal plane array, wherein each column of pixels in one of the spatially separated areas represents a wavelength contained within an associated one of the plurality of sample emissions.

In another aspect of this disclosure, an apparatus is provided for simultaneously collecting, processing, and displaying IR spectral information for one or more samples. The apparatus includes a plurality of IR light sources; at least one optically dispersive element; a plurality of optical paths; an IR FPA; processing means for processing an output of the IR focal plane array and determining the IR spectral information; and display means for displaying the IR spectral information, wherein each of the plurality of IR light sources presents a different angle of incidence with respect to the one or more samples, wherein each of the plurality of optical paths directs an associated one of a plurality of reflected IR beams to a different spatial area on the IR FPA.

In another aspect of this disclosure, a method of determining anisotropic IR optical constants of a material is provided. The method includes providing a substrate; projecting an IR light source onto a surface of the substrate at a non-perpendicular angle of incidence; transmitting a first transmitted portion of the IR light source through the substrate; coupling the first transmitted portion of the IR light source through an optical path and onto a first area on the FPA; providing a film material on the substrate; projecting the IR light source onto a surface of the film material at the non-perpendicular angle of incidence; transmitting a second transmitted portion of the IR light source through the film material and the substrate; coupling the second transmitted portion of the IR light source through the optical path onto a second area on the FPA; rotating a mirror in the optical path to move the second area on the FPA so as to coincide with the first area on the FPA; and determining an angle of refraction within the film material by measuring an angle of rotation of the mirror.

There are a variety of ways to minimize the problem of water vapor compensation during measurement of IR sample spectra. In yet another aspect of this disclosure, a Planar Array Infrared Reflection-Absorption Spectroscopy (PA-IRRAS) arrangement for measuring an orientation of a thin film on a substrate is provided, which includes an IR source; two orthogonally polarized filters which receive an IR light beam from the IR source; a PAIR detector; and a processor, wherein two orthogonally polarized IR beams emanating from the two orthogonally polarized filters are reflected from the thin film and detected by the PAIR detector, wherein a differential reflectivity spectrum is calculated by the processor, and wherein the differential reflectivity spectrum is substantially free of any polarization-independent signals including water vapor absorptions, instrumental drifts, and signal fluctuations. The processor then uses the calculated differential reflectivity spectrum to determine a molecular orientation of the thin film.

In a related aspect, a method of determining an orientation of a thin film on a substrate is provided, which includes providing an IR source; producing two orthogonally polarized light beams from the IR source; reflecting the two orthogonally polarized light beams from the thin film, detecting the two reflected orthogonally polarized light beams with a PAIR detector; and calculating a differential reflectivity spectrum in the processor using the two reflected orthogonally polarized light beams, wherein the differential reflectivity spectrum is essentially free of any polarization-independent signals including isotropic water vapor absorptions, instrumental drifts, and signal fluctuations.

In the various aspects of this disclosure, either direct lens coupling through an aperture, or through mid-IR optical fibers, for example, may be used to collect sample light emissions representing the samples. Use of optical fibers may provide desired flexibility in placement of the apparatus, and allow remote sensing of, for example, smokestacks, and also allow easier implementation of multiple channel detection and chemical analysis.

The apparatus and method of this disclosure do not require moving parts to determine spectral information. The method and apparatus are, consequently, well adapted to relatively harsh environments, such as, for example, high vibration environments in a manufacturing plant, or temperature extremes, as might be found in the field.

At least partially as a result of the no-moving-part construction, the method and apparatus may also be used in various industrial applications to measure and detect the thickness, either in transmission or reflection mode, the chemical structure and orientation of coatings/films (solid, liquid, chemically bound, physically adsorbed) on liquid surfaces, including but not limited to water, oil and other solvents, and also to measure the thickness, orientation and chemical structure of films electrochemically deposited on solid substrates, including but not limited to metals and semiconductors.

The multi-beam PAIR spectrograph offers numerous advantages over conventional FT-IR interferometry for a variety of important materials characterization applications, including routine IR spectroscopy, time-resolved IR spectroscopy, time-resolved spectroscopic imaging, mono-layer spectroscopy, on-line monitoring of processes in aggressive environments, and probing fundamental dynamics associated with thick and thin polymer films un-dergoing an irreversible change.

DESCRIPTION OF THE DRAWINGS

The features and advantages of this disclosure will be more readily understood upon consideration of the following detailed description, taken in conjunction with the accompanying drawings in which:

FIG. 3B depicts another aspect of the present invention in which non-interferometric IR spectroscopy of multiple samples is accomplished using multiple IR sources and optical paths, and no moving parts;

FIG. 3C shows further optical path details for an arrangement suitable for the spatial multiplexing of multiple beams for the apparatus depicted in FIG. 3B;

FIG. 3D shows sampling with polarized light;

FIG. 4 shows another aspect f the invention using a Pellin-Broca prism as the optically dispersive element, and which shows IR optical fiber being used to couple the light into the apparatus;

FIG. 11 shows an arrangement of the invention suitable for Planar Array Infrared Reflectance-Absorbance Spectroscopy (PA-IRRAS).

DETAILED DESCRIPTION

Figure 1:
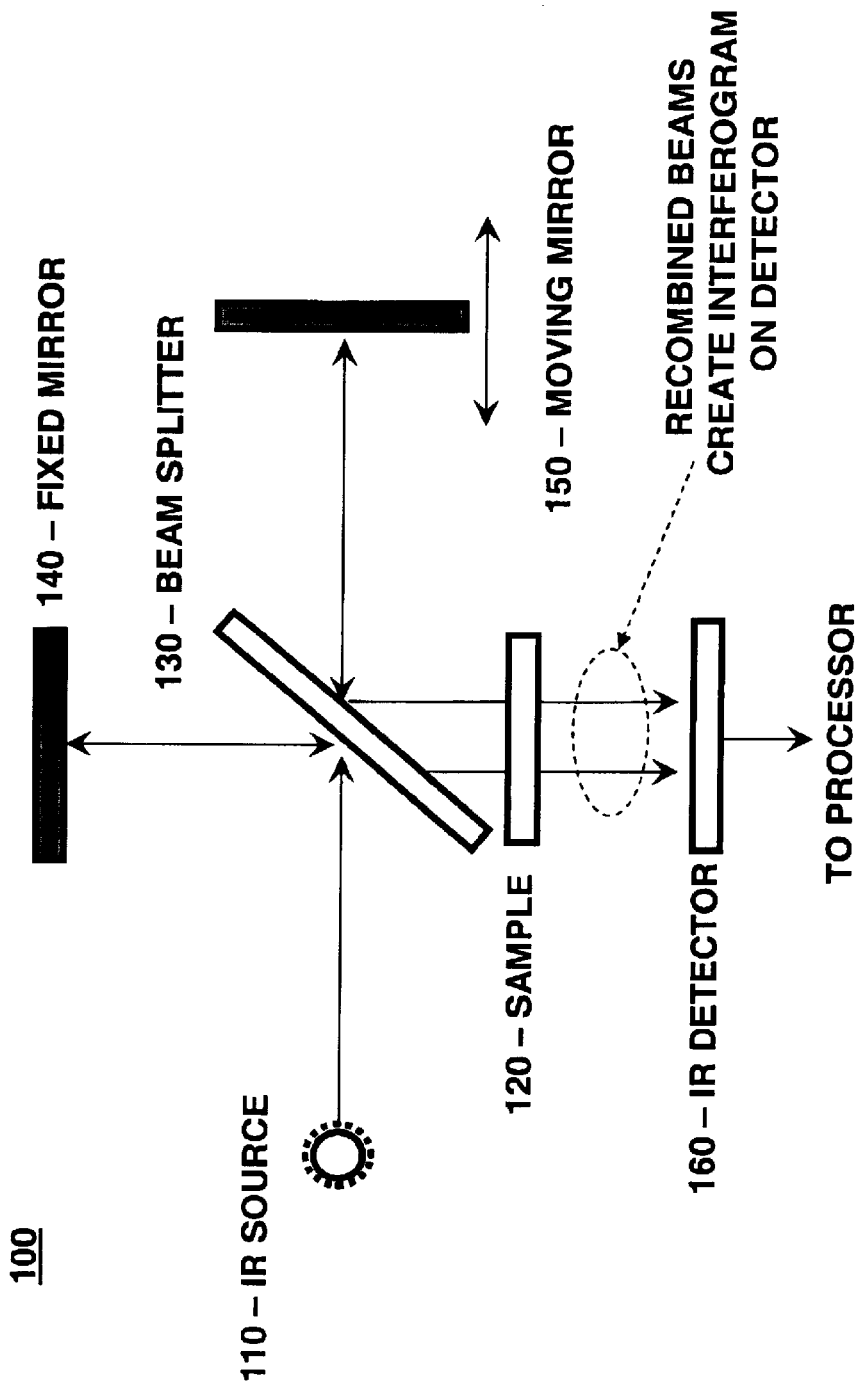
FIG. 1 provides a representation of a conventional FTIR interferometer.
Figure 2:
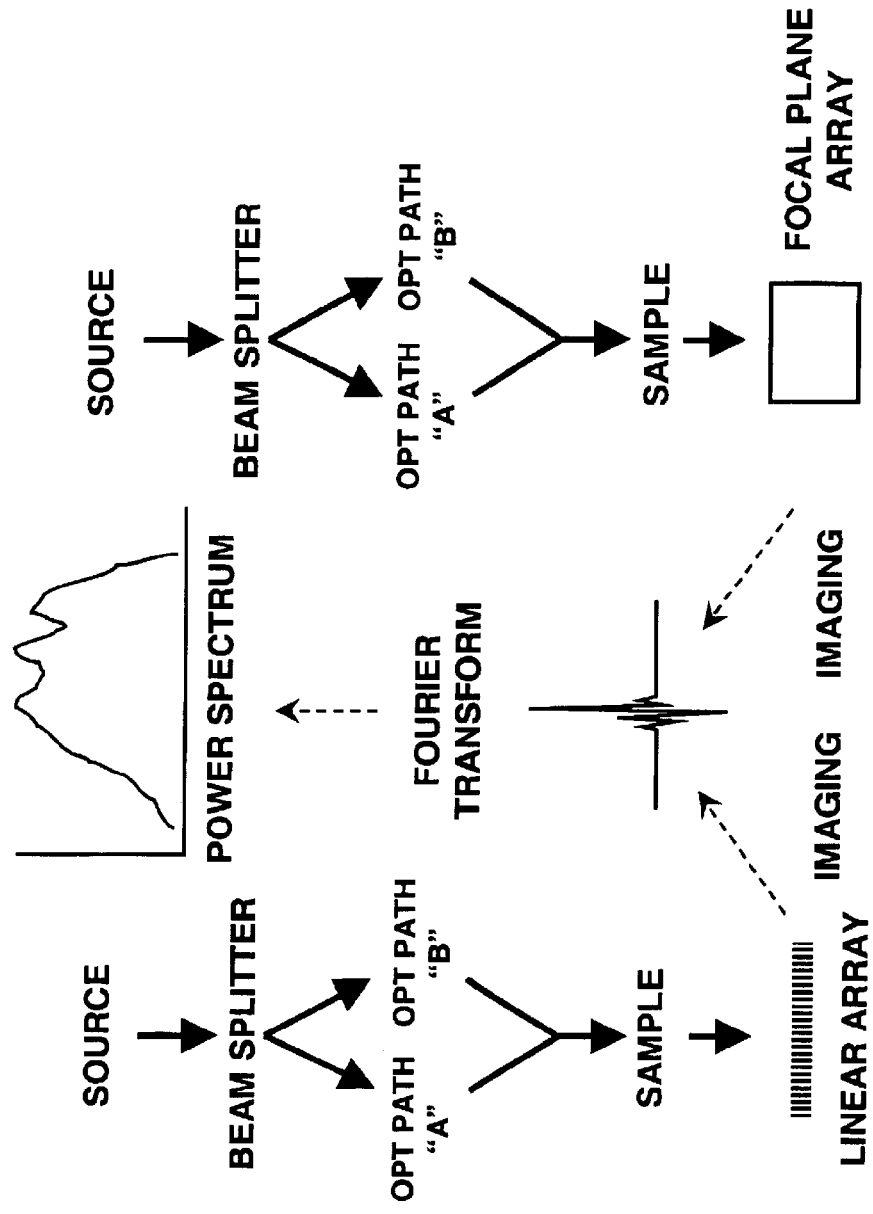
FIG. 2 provides two different schemes used for conventional interferometry based on Fourier Transform, but which do not require moving parts to generate a difference in optical path length.
Figure 3A:
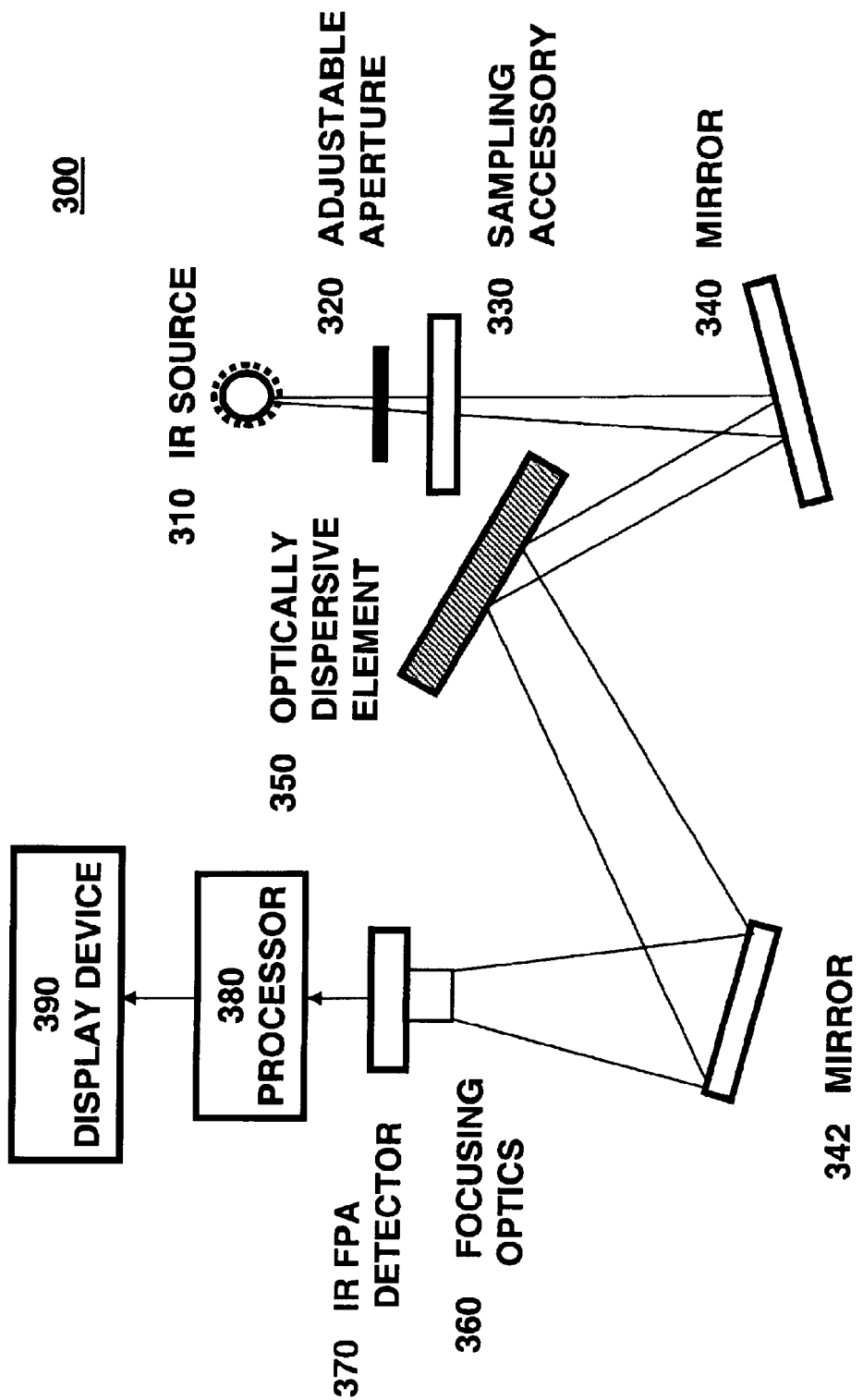
FIG. 3A depicts an aspect of the present invention suitable for non-interferometric IR spectroscopy of multiple samples in one sample holder is accomplished using no moving parts.

A first aspect of this disclosure will be explained with reference to FIG. 3A. Apparatus 300 includes an IR light source 310, which may be any common IR light source, including, for example, tungsten lamps, Nernst glowers, or glowbars or, in some applications, IR radiation from the sun may be used. In a preferred embodiment, the IR source may be a IR Emitter with ZnSe window, manufactured by Cal-Sensors, for example. Ideally, IR source 310 has a "flat" or uniform intensity across the IR spectrum, or at least a portion of the IR spectrum. However, if IR source 310 is not uniform, such non-uniformity may be accounted for during the analysis process.

Adjustable aperture 320 is used, at least in part, to establish the resolution of the apparatus, i.e., a smaller-sized opening provides higher resolution. Adjustable aperture 320 may be a circular iris or, in a preferred embodiment, an adjustable rectangular slit, having a length dimension, for example, of approximately 1 cm, and an adjustable width of 0–2 mm. Such a slit is manufactured by RIIC, as model WH-01.

Sampling accessory 330 positions one or more sample volumes, which contain one or more samples to be analyzed, in the optical path. Sampling accessory 330 may be, in a preferred embodiment, a simple sample holder, which merely positions a small sample volume of material to be sampled, e.g., polymer film, near IR source 310, or it may comprise a more elaborate sampling volume arrangement known and used for sampling gases, or may hold a plurality of samples.

Gases, which have a lower density than solids or liquids, may require such a relatively more elaborate sampling accessory having a set of mirrors or other suitable arrangement (not shown) to provide for multiple passes of the IR source through the sample volume. Such multiple passes are useful in ensuring that sufficient optical density is achieved for the IR absorption phenomena to be reasonably measured. Multiple pass arrangements may also be used, in other embodiments, to monitor smokestack emissions, or to monitor hazardous chemical fumes or vapors in laboratory, military, or industrial environments.

Sampling accessory 330 could also comprise optics including a telescope or microscope arrangement, or coupling to a single optical fiber or bundle of optical fibers.

Turning now to FIG. 3B, apparatus 300' may include a plurality of sampling accessories 330, 331 (or more) that may be used, along with appropriate optics, to pass a portion of an emission from IR source 310 through sampling accessory 330, and a portion of an emission from second IR source 311 through aperture 321, and sampling accessory 331.

Optically dispersive element 350 receives portions of an emission from IR light sources 310 and 311 that are passed through respective sample volumes, and reflected from mirrors 340 and 341. The entire IR spectrum, representative of IR source 310, may not be passed through the sample volume because of the absorption of one or more IR wavelengths in the sample volume within sampling accessory 330. The non-absorbed IR wavelengths then interact with optically dispersive element 350 to form a dispersed light beam, which separates or spreads, in one direction, the wavelengths present in the IR light exiting sampling accessory 330.

Optically dispersive element 350 may be, in one aspect of this disclosure, a ruled diffraction grating having 300 lines (or "grooves") per mm, with a blaze wavelength of 4.0 $\mu$m, for example. Such a grating is manufactured, for example, by SPEX, as model 300 g/mm Holographic Grating. Although not shown, there may be two optically dispersive elements, appropriately arranged in one or more associated optical paths. The second optically dispersive element may have, for example, 50 grooves per mm, and a blaze wavelength of 9.0 mm, to allow two different spectral regions to simultaneously be collected on the FPA, to more efficiently use more of the surface area of the FPA for signal analysis, and to allow for simultaneous analysis of multiple signals.

Figure 5:
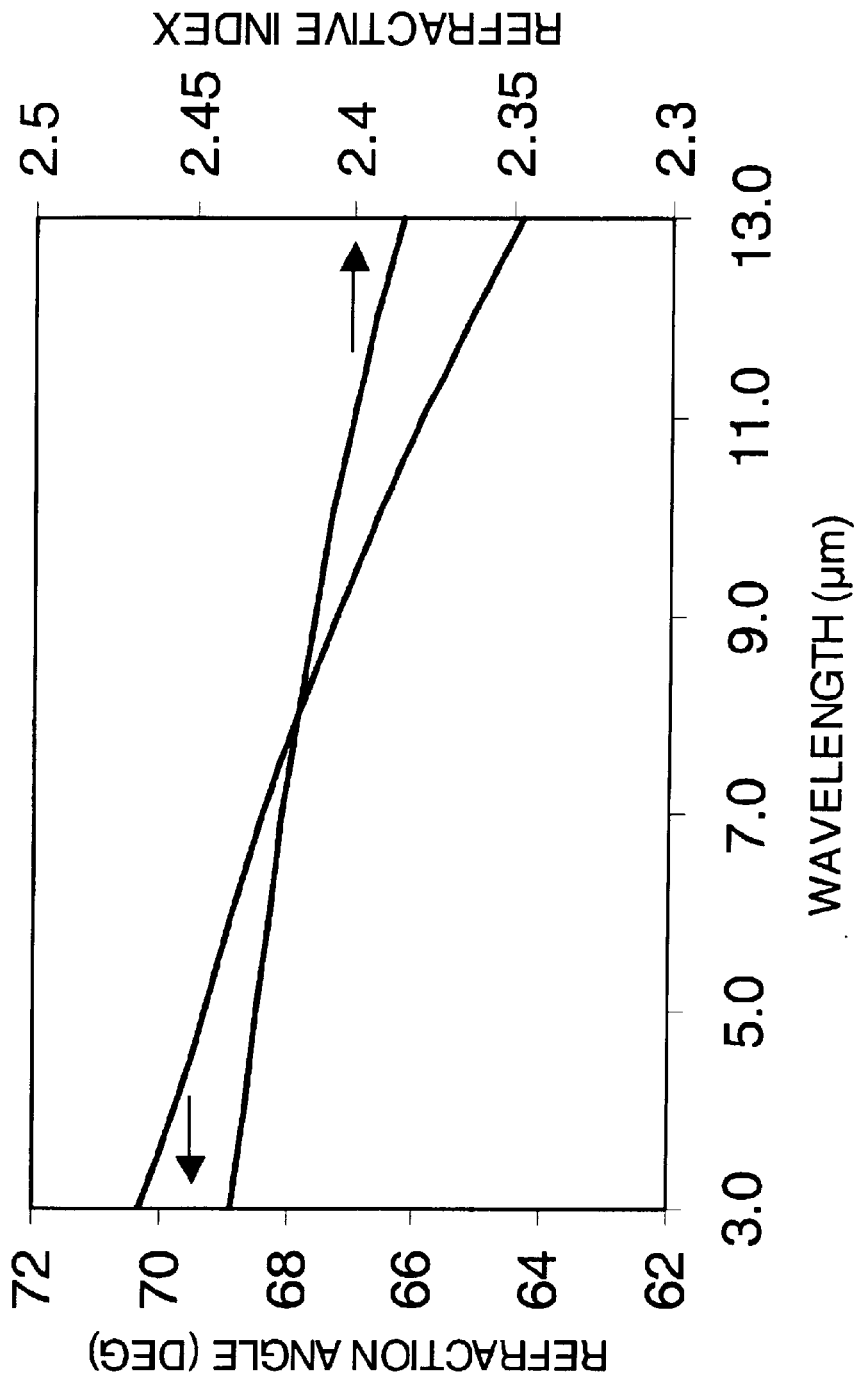
FIG. 5 provides a graph of refractive index dispersion of ZnSe, and optical refraction for the Pellin-Broca prism of FIG. 4.

In another aspect, the optically dispersive element may be a prism, as shown in FIG. 4. In a further preferred aspect of this embodiment, Pellin-Broca prism 450 may be used. In IR wavelengths, the Pellin-Broca prism may be machined from zinc selenide (ZnSe) in order to minimize the material absorption in these IR spectral ranges, and to ensure adequate optical dispersion as a function of wavelength. FIG. 5 provides a graph of refractive index dispersion of ZnSe and optical refraction for an exemplary embodiment of the Pellin-Broca prism of FIG. 4. Apparatus 400 operates similarly to apparatus 300 shown in FIG. 3A, however variations in components are optionally present.

For example, a light coupling means may include IR fiber 410, which may also include a multi-fiber bundle; off-axis parabolic mirror 440; concave mirror 442; and convex mirror 444. The light being projected by IR fiber 410 may include light coming from the sample volume being illuminated, or the IR fiber may be used to illuminate the sample volume. Focusing optics 360 may be, in this embodiment, a germanium (Ge) condensing lens used to properly project the light emanating from prism 450 onto IR detector 370. The parabolic-shaped mirrors are preferable when using an IR fiber, in order to collimate the cone-shaped fiber output light beam. The Pellin-Broca prism may also be used with the optical coupling and IR source 310 in FIG. 3, as well as in the fiber optic implementation. Conversely, the ruled diffraction grating may be used with fiber optics, assuming that appropriate measures are taken to collimate the conical beam emanating from the fiber, and to couple the light into the system, and onto the diffraction grating, when used as optically dispersive element 350.

Although a diffraction grating can provide adequate resolution for many application, the Pellin-Broca geometry may provide three benefits: (1) optical dispersion is only a function of the refractive indexes at different wavelengths, thus simplifying the optical design; (2) the two-in-one prism design has a very high angular dispersion efficiency, and the approximate 90° beam folding available allows a compact footprint of the optical system to be achieved; and (3) a Brewster angle incident configuration may be utilized in order to maximize the transmission of light at the ambient/ZnSe interface. The latter is crucial in the IR range where reflection loss is a major concern due to the high refractive index of ZnSe (~2.4).

Based on a ray-tracing calculation with the refractive mdcx information shown in FIG. 5, a 67.5° Pellin-Broca prism made of ZnSe operating in the "short-side entrance" geometry at approximately the Brewster angle ($\theta_B$ of ZnSe~67°) will give angular dispersion of about 6° between the 3 and 13 $\mu$m wavelength beams. The on-chip spatial separation between the different wavelengths is determined by the focusing optics used, the size of the Pellin-Broca prism, and the f-number of the system. A span of between 500 to 1000 cm$^{-1}$ of the spectral range may be focused onto the FPA horizontally (256, 320, etc. pixels). Given the number of pixels in the FPA along the dispersion direction of the optical beam, the maximum resolution is about 5 cm$^{-1}$. However, using different optical components, such as a finer grooved grating, for example, a resolution of better than 5 cm$^{-1}$ is readily achievable for this spectrometer.

Besides the Pellin-Broca prism design, special diffractive gratings optimized for mid-IR performance, can theoretically provide similar, if not better throughput and dispersion than a prism approach. However, the dependence of resolution on both the groove number and grating size may put more constraints on the optical design using gratings. Therefore, there are trade-offs to be considered when considering the use of gratings versus prisms. Relatively low-cost off-the-shelf gratings with low groove numbers may suffice for many applications, and in situations where higher resolution is required than can be currently obtained with prisms.

In either case of using a prism or a diffraction grating, optically dispersive element 350 may be adjustable with respect to an angle of incidence between its surface and incident light which is projected onto the surface. Such an angular adjustment may be used to control the wavelength range, or spectral bandpass that is presented to IR detector 370, discussed below.

Focusing optics 360 couples light from optically dispersive element 350 into IR detector 370 which has a plurality of detection elements arranged at least along a dispersion direction corresponding to the direction of the dispersed light beam. Typically, incident light is projected onto more than one row of pixels, and the projected light from the optically dispersive element may cover 20 pixels. IR detector 370 detects the dispersed light beam from optically dispersive element 350, and provides an output, which is subsequently used to determine the IR spectral information of the sample in the sample volume contained in sampling accessory 330.

In one aspect of this embodiment. IR detector 370 may be an InSb camera sensitive in the 3–5 $\mu$m wavelength range, for example, Merlin Mid model, manufactured by Indigo Systems. Such a detector includes a 320×256 pixel InSb detector, with 30 $\mu$m pixel pitch; a 3.0–5.0 $\mu$m changeable cold filter; user selectable frame rates of 15, 30 or 60 frame-per-seconds (fps) (minimum); a liquid nitrogen cooled dewar, having a minimum hold time of 4 hours; a noise equivalent temperature difference NE$\Delta$T<20 mK; user selectable integration times from 10 $\mu$s to 16.6 ms; and corrected nan-uniformity <0.1%. InSb detectors in this range may also be thermoelectrically cooled to enhance portability.

This particular InSb camera may be controlled via on camera controls or via an RS-232 interface with a vendor supplied Graphical User Interface, or standard Windows® terminal communications program, or commercially available interfaces such as Universal Serial Bus (USB) or IEEE 1394 standard interface. In addition, this camera provides an automatic gain control (AGC) algorithm, adjustable detector gain and bias to allow viewing of both high and low brightness scenes, and data outputs which may include NTSC, S-Video, and 12 bit corrected digital video. In addition, focusing optics 360 may be provided along with IR detector 370; the above-described InSb detector is commercially available with a 25 mm mid-IR lens.

In another aspect, IR detector 370 may be a microbolometer camera, also manufactured by Indigo Systems as model Merlin Uncooled. This particular camera includes a 320× 240 pixel niicrobolorneter detector having 51 $\mu$m pixel pitch in a 7.5–13.5 $\mu$m spectral range. User selectable frame rates of 15, 30 or 60 fps (minimum) are available. This device, in contrast to the TnSb camera, is thermoelectrically (TE) stabilized at 313K; has a noise equivalent temperate difference NE$\Delta$T<100 mK: and has user selectable integration times from 1–48 $\mu$s.

This detector array may be controlled in the same manner as for the InSb array, as discussed above. Similar detector gain controls, and data outputs are available, as in the InSb model.

Further, in yet another embodiment, mercury-cadmium-telluride HgCdTe ("MCT") array may be used as IR detector 370, and has improved sensitivity and bandwidth in comparison to the InSb and microbolometer devices. Presently, such arrays are somewhat difficult to manufacture, and are more expensive than other available IR detectors. Using an available MCT FPA having a maximum frame rate of 6000 Hz, a single beam spectrum may be collected every 170 $\mu$s, and integration times as low as 10 $\mu$s are achievable.

Although both InSb and microbolometer types of detectors may be cooled thermoelectrically, the sensitivity of the InSb FPA is much higher than that of the microbolometer FPA. As a matter of fact, the sensitivity for the InSb FPA identified above is better than a liquid nitro-gen-cooled MCT detector commonly used in traditional FTIR. On the other hand, the sensitivity of the state-of-the-art microbolometer-based FPA is still about one order of magnitude lower than that of liquid nitrogen-cooled MCT detector. However, sensitivity at the performance level of a liquid nitrogen-cooled MCT detector is not always necessary and, for many applications, it is possible that the lower sensitivity of the microbolometer FPA will not cause any significant efficiency problems in the apparatus. In addition, the key advantage of using an FPA, when compared to single element detector, is the possibility of vertical binning. By adding the signal from a finite height of pixels, SNR can be significantly improved.

An optical path or light coupling means between the various elements in apparatus 300 may include, in one aspect, standard IR mirrors 340, 341, 342 of various configurations to couple light from IR sources 310, 311 through the sample volume in sampling accessories 320, 321 onto or thru optically dispersive element 350, and onto IR detector 370 through focusing optics 360. This configuration could include multiple sampling accessories or polarizers, for example. The mirrors may include, for example, 3-inch (~7.6 cm) diameter front surface aluminum mirrors, manufactured by Newport Corporation. Other mirror coatings available for use in the IR band may be, for example, copper, and gold.

Turning to FIG. 3C, more details of the arrangement shown in FIG. 3B are shown. For example, the beam optics may be arranged and adjusted to present the images from each of the samples to a different position on optically dispersive element 350. This results in, effectively, partitioning IR FPA detector 370 into different regions for each of the sample emissions, or for different spatial areas of one sample. Further, such partitions could be used with additional IR sources and/or samples. Known methods could be used to address selected rows and/or columns of the FPA, for example.

The emission from either or both IR light sources 310 and 311 may also be arranged to interact with a background reference environment arranged along the optical path to provide a background reference emission, and the IR FPA detector detects the resulting dispersed background reference light beam on a spatially separated area form the emissions representing the samples.

The processor may receive an output from the FPA including a signal representing the dispersed background reference light beam and, essentially in real time, determines compensated IR spectral information for each of the plurality of samples by compensating for the background reference environment.

In another aspect, and with reference to FIG. 3D, first and second polarizers 335, 336, orthogonally polarized with respect to each other, are placed in the optical path to receive separate IR emissions, which could be, for example, provided by IR light sources 310 and 311. The resulting polarized beams both pass through the sample held by sampling accessory 330, for example, and resulting first and second polarized sample emissions are coupled along one or more optical paths to interact with optically dispersive element 350, and are projected onto FPA detector 370. Alternatively, a beam splitter (not shown), in conjunction with the polarizers, may be used to obtain two orthogonally polarized light beams from one IR source beam.

The first polarized sample emission may orthogonally polarized with respect to the second polarized sample emission. These orthogonally polarized light beams may be used to determine a molecular orientation of a polymer film by comparing the intensities of each of the polarized beams to each other, or to empirical standards.

As mentioned previously, the IR FPA detector may detect each of the corresponding plurality of dispersed sample light beams on spatially separated areas of the IR FPA detector.

In all aspects of this disclosure, the IR FPA detector simultaneously detects the corresponding plurality of dispersed sample light beams, and the at least one output of the FPA determines the IR spectral information for each of the plurality of samples at a same instant in time. Further, the FPA may comprise InSb, HgCdTd (MCT), or a microbolometer FPA, and detects light having a wavelength at least in a mid-IR band.

In another aspect of this disclosure, theIR FPA detector comprises an IR camera. An InSb focal plane array (FPA) may be used to detect absorplions in the 3–5 $\mu$m range, while a microbolometer-based FPA may be utilized for the 7–13 $\mu$m range. Further, a MCT array, or other InSb or other type of array having a wider or different spectral response may be used. Further, the at least one output from the IR FPA detector includes a plurality of summed pixel outputs at each of a plurality of wavelengths present in the dispersed light beam. The plurality of summed pixel outputs at one of the plurality of wavelengths improves a signal-to-noise-ratio of a signal representing an intensity of said one of the plurality of wavelengths.

In another aspect, the IR FPA detector may be partitioned into multiple segments each containing a different subset of the multiple pixels. Each of the corresponding plurality of dispersed light beams may be projected onto an associated one of the multiple segments. The "partitioning" of the IR FPA is not necessarily intended to imply an actual physical partitioning realized in hardware, per se, but may be implemented using known techniques for addressing particular rows and columns of pixels on the IR FPA using a relatively simple software control interface between the processor and the IR FPA.

In all aspects of this embodiment, the corresponding plurality of dispersed sample light beams may be projected onto the IR FPA detector such that a row direction on the IR FPA detector is essentially aligned with a dispersion direction of said each of the corresponding plurality of dispersed sample light beams. Each column of the focal plane array, within each of the multiple segments, corresponds to a particular wavelength of light contained in the plurality of dispersed sample light beams.

Further, within at least one of the multiple segments, an output from one pixel in each of a plurality of rows may be added together along one column of the focal plane array to improve a signal-to-noise-ratio of a signal representing an intensity of an associated wavelength of light.

Further, in another aspect of this disclosure, dispersed sample light beams associated with different spatial sections of one of the plurality of samples may be projected onto two or more of the multiple segments. Different wavelengths may be represented within at least two of the multiple segments, whether imaging different spatial sections of one sample, or imaging different samples in the multiple segments.

In another aspect, at least one of the plurality of samples may include a background target containing an analyte.

The analyte may be selected to react to a specific type of biological agent to produce an IR absorption change in the background target.

For example, the analyte may be a bio-specific reagent reactive to one or more biohazardous materials, for example, a virus or bacteria. Further, an audible or visual alarm, or both, may be activated when the bio-specific reagent reacts to any biohazardous materials.

As discussed with reference to FIG. 3B, the at least one sample holder or accessory includes a plurality of sampling accessories, each of said plurality of sampling accessories positioning a different sample volume in the optical path. The apparatus is capable of simultaneously determining IR spectral information for each of the different sample volumes. The sample holder may be configured to provide an optical path for each of the plurality of samples that is suitable for detection of an IR absorption phenomenon within the optical path.

In another aspect, a plurality of optically dispersive elements 350 (not shown) may be provided to form a plurality of dispersed light beams, each corresponding to a different sample. Each of the plurality of dispersed light beams may be projected onto a different spatial area on the IR FPA detector 370.

In one aspect, a display for displaying an IR spectrograph for one or more of the plurality of samples, and means for controlling the IR FPA detector and the display may be provided. The means for controlling the IR FPA detector and the display may include at least a processor or a personal computer.

Further, in a transmission mode, IR light source 310, 311 may be transmitted through each of the plurality of samples along the optical path. In a reflectance mode, the emission from the IR light source may be reflected from each of the plurality of samples along the optical path.

In another aspect of this disclosure depicted in FIG. 4, the optical path may include the use of an optical fiber or optical fiber bundle, particularly multimode IR optical fibers, such as, for example, fiber model C1-500 manufactured by Amorphous Materials, Inc. Different sample types and sampling geometry may advantageously allow a mid-IR optical fiber to be incorporated between the source and dispersing element to deliver the IR source to the sample volume, and to provide an optical path for the IR light after absorption in the sample volume to the dispersive element.

Optical fibers with loss below 1 dB/m in the mid-IR range (including the 3–5 or 7–13 $\mu$m range), are commercially available. These multimode fibers offer features such as flexibility and ease-of-use as found in their fiber counterparts in the visible and near-IR range. The thermal and mechanical properties of these optical materials have been improved dramatically over the past decade.

When combining a FPA detector and a multichannel fiber bundle, simultaneous measurements of several samples, or the same sample at different locations, become possible. This means that the proposed spectrometer can offer multiple detection channels with a single instrument, therefore dramatically reduce the cost-of-ownership on a per channel basis. In the general design scheme shown in FIG. 4, off-axis parabolic mirror 440 is utilized to collect and collimate the signals from either the entrance aperture or an output end of IR fiber 410 or fiber bundle. An adjustable aperture 420 may be used to control the size of the collimated beam, and subsequent condensing optics 442, 444 are used to couple the signal into the prism. The combination of the beam condensing optics and aperture size determines the f-number of the spectrometer, and therefore the spectral resolution.

Processor 480 may be a special purpose computer adapted specifically for IR spectral processing, and may be implemented in so-called "firmware" or integrated circuits such as a custom application specific integrated circuit (ASIC), or may be a common personal computer (PC). Processor 480 may provide control software/hardware for IR detector 470.

In an aspect of this disclosure using any one of the FPAs discussed above, "Talon Ultra" Data Acquisition System, manufactured by Indigo Systems may be used. Processor 380 may be implemented as a dedicated IR image acquisition station which includes a 500 MHz Pentium® III PC, 256 MB RAM, 12 GB hard drive, Windows® NT 4.0 operating system, IR camera digital interface cable (10 ft, or ~3 m), high speed 16 bit frame grabber, camera interface software, and image analysis software based on Image Pro® 4.0 or equal. Such an exemplary package provides a full range of utilities for processing, measuring, analyzing, and outputting images to capture, study, manipulate, and store images and data from the IR camera.

Display device 390 may be either a standard computer monitor such as a CRT or LCD display, or may be a printing device.

Although this particular exemplary embodiment may use the PC system memory for data acquisition, a special-purpose, dedicated high-speed memory may also be utilized (not shown). For added portability, processor 380 of 480 may be incorporated into a laptop or notebook computer, with an integral LCD display.

In an exemplary embodiment, software running on processor 380 or 480 may provide a wide variety of features such as real-time histograms; real-time digital filtering; real-time frame averaging, a user definable region-of-interest (ROI); full-featured data display, reduction, analysis capability; and Visual Basic-compatible macro language for automating data collection, analysis, and reporting.

In this type of application, "real-time" may be construed to be less than one second, from initialization, through sampling and analysis, or may even be construed to mean less than 500 ms, or even less than 20 ms. This type of response time provides favorable results over the conventional scanning and interferometric techniques. Further, "real-time" detection indicates the ability to continuously monitor a process as it happens, where the time domain between collected data sets, or duty cycle is, in general, in the 5–100 $\mu$s range.

Additional analysis software may operate in processor 380, 480 to analyze the IR spectral information, and to determine one or more specific functional groups found in the sample volume, e.g., fluorocarbons, hydrocarbons, or complex molecular bonds or "signature" functional groups, such as those found in chemical or biological warfare agents. Further, an alarm, either audible or visual, or both may also be activated if a particular signature functional group or chemical composition is determined to be in the sample volume.

Although some components of apparatus 300, 400 are adjustable to facilitate setup or to provide for optimal data collection, it should be noted that apparatus 300, 400 are capable of determining IR spectral information using no moving parts whatsoever during operation.

The non-interferometric apparatus of the first embodiment is operated to determine an IR spectrum of a sample in a sample volume by providing an IR source; positioning the sample volume in the optical path; passing at least a portion of an emission of the IR source through the sample volume and into the optical path; optically dispersing at least a portion of an emission of the IR source to form a dispersed IR light beam; detecting the dispersed IR light beam using the plurality of detectors; and non-interferometrically determining the IR spectrum of the sample by evaluating an output from the plurality of detectors. In a more preferred method, a two-dimensional detector array, such as a FPA, for example, is operated, wherein each column of detectors represents a wave-length contained within the dispersed IR light beam, and at least two rows of detector elements are used to improve a SNR of the detected signal.

Before the apparatus may reliably be used, IR sources 310, 311 must be calibrated, or at least the spectral intensity across the band of interest must be known, in order to compensate for possible non-uniform source intensity.

Conventionally, the source calibration process included a serial process of collecting the background power spectrum without a sample volume in the optical; collecting the sample power spectrum; and then dividing (or forming a ratio of) the sample power spectrum by the background power spectrum to determine the sample intensity/background intensity, or transmission, for every frequency position reported by the apparatus. Customarily, the data is further processed by a logarithmic operation, i.e., determining the absorbance spectrum (ABS), as $$ABS \propto -\log_{10} (sample/background).$$

However, with the multi-beam approach of this disclosure, source and environment calibration may be carried out simultaneously with sample emission detection. Processors 380, 480 then compensate the sample measurements essentially in real-time, using the source and environment calibration data.

Once an absorbance spectrum has been determined, the disclosed apparatus and method may be used in industrial or environmental process monitoring to measure a thickness of a solid or liquid film or coating on another solid or liquid, for example.

Based on the general operation procedures describe above, the absorbance spectrum of a sample is obtained using this disclosure. The quantity of absorbance (ABS) can be expressed, in general, as follows:

$$ABS = A \times B \times C,$$

where A is the absorption coefficient of the absorbing functional groups present in the sample; B is the path length within the sample (thickness), and C is the concentration of the functional groups. This quantitative relation is widely known as "Beer's Law".

Concentration and thickness measurements can be made using a standard sample with known concentration C and known thickness B, to calculate the absorption coefficient A for any vibrational band shown by that sample. Once A is known for the absorption band, one then can use Beer's Law to measure either the concentration or the thickness.

For example, in a film processing line, if the material formulation is held constant, then the corresponding C and A values are also constant. In this case, one can use this disclosure to monitor the film thickness, since the absorbance level is directly proportional to B. On the other hand, in a semiconductor chemical vapor deposition (CVD) processing chamber, for example, the concentration of the gaseous species can be measured by this disclosure since A (a known species) and B (a fixed chamber size) are held constant, leaving the concentration to be determined as being directly proportional to the measured absorbance.

Orientation measurements are made in the following way. When non-polarized IR light is used in IR measurements, all functional groups with the matching vibration frequencies will cause absorption. However, when the incident IR light is linearly polarized so that only electromagnetic waves oscillating in a particular direction are passed, then only the functional groups having both matching frequencies and a dipole moment change in the same direction as the polarized light can absorb the incident light.

For randomly oriented samples, all dipole directions are equally sampled, and therefore no dependence on the polarization direction would be observed. On the other hand, for samples with preferred orientation caused by processing steps, there would be much stronger absorbance when the polarization direction matches that of the sample dipole change direction. By comparing the absorption spectra with polarized and non-polarized IR light, one can deduce to what extent the sample under study is oriented, and in which direction.

The polarization of infrared light is often accomplished with the use of a gold wire polarizer. This optical device may be composed of, for example, finely separated gold wires arranged in parallel on a IR transparent substrate, such as ZnS.

The quantitative relation between the polarization direction and the sample dipole direction is depicted as follows:

$$ABS_{Observed} \propto \cos(\theta),$$

where T is the angle between the sample's dipole moment change direction during the vibration, and the polarization direction of the incident IR light. From the above relation, one can see that, when T=90°, there will be no absorption, even if the vibration frequency condition is satisfied.

In another aspect of this disclosure, a method further includes adjusting an optical dispersion of the plurality of sample emissions to control a range of wavelengths in the plurality of dispersed sample beams. Typically, an angle of incidence on either optically dispersive element 350, e.g., a grating, or prism 450, e.g., a Pellin-Broca prism, is adjusted to vary the range of wavelengths presented to the IR FPA 370, 470.

The method may further include increasing a signal-to-noise-ratio by co-adding a plurality of pixel outputs in said each column of pixels in one of the spatially separated areas.

As previously mentioned, in another aspect, the method includes simultaneously evaluating a reference spectrum of an environmental background; and correcting the IR spectrum of each of the plurality of sample to account for the reference spectrum of the environmental background.

The method may also include simultaneously evaluating a spectrum of the IR source; and correcting the IR spectrum of each of the plurality of sample to account for the spectrum of the IR source.

In another aspect, the method may include processing the IR spectrum of each of the plurality of sample emissions to identify one or more signature functional groups in the plurality of sample volumes; and enabling an alarm if one or more signature functional groups, for example, a chemical or biological warfare agent, are found in any one of the plurality of sample emissions.

In this regard, the method may include providing a background target having a bio-specific reagent thereon; and reacting the bio-specific reagent with a sample volume containing said one or more signature functional groups.

In another aspect of this disclosure, a method further includes maintaining the broadband light source, the optically dispersive element, and the two-dimensional IR detector array relatively motionless at least with respect to each other at least during said steps of projecting, interacting, coupling, forming, and optically coupling steps.

The optical coupling step may include fiber optic coupling of the sample light emissions, and/or the projecting step may include fiber optical coupling a portion of the emission of the broadband light source into the plurality of sample volumes.

In yet another aspect of this disclosure, the method may further include determining, from the IR absorption spectrum of one or more of the plurality of samples, at least one physical attribute of the one or more of the plurality of samples, wherein at least one physical attribute is continuously determined essentially in real-time. The physical attribute may include a molecular orientation of one of the plurality of samples, for example, which is accomplished, at least in part, by comparing two orthogonally polarized sample emissions associated with said one of the plurality of samples. The physical attribute may also include measuring a thickness of a film in real-time, in particular, a monolayer polymer film.

Further, each of the plurality of IR light sources 310, 311 may have a different intensity and, in another aspect of this disclosure, one or more of the optical paths may include a polarizing element.

In another aspect, the processing means may be used to ascertain a molecular orientation of a monolayer, including a polymer monolayer, from IR spectral information determined from the different spatial areas on the IR FPA, particularly where orthogonally polarized sample emissions are evaluated.

In another aspect of this disclosure, the method further includes computing a refractive index and an absorption coefficient of the film material. The substrate may include a dielectric substrate having known optical properties, as used in semiconductor processing, for example. The monolayer film also may be adsorbed on the substrate.

In this aspect, the method may further include projecting the IR light source onto a surface of the substrate at a plurality of non-perpendicular angles of incidence; and determining the angle of refraction within the film material by measuring the angle of rotation of the mirror for each of the plurality of non-perpendicular angles of incidence.

In addition, polarized IR radiation may be projected through the film material and the substrate; directionally specific angles of refraction within the film material may be determined; and the directionally specific complex indices of refraction of the film material may be computed.

Further in this regard, a molecular orientation of at least one molecular group in the film material may be determined.

Using the PAIR spectrograph apparatus and method of this disclosure it is possible to perform external reflection measurements with real time background compensation.

Figure 6:
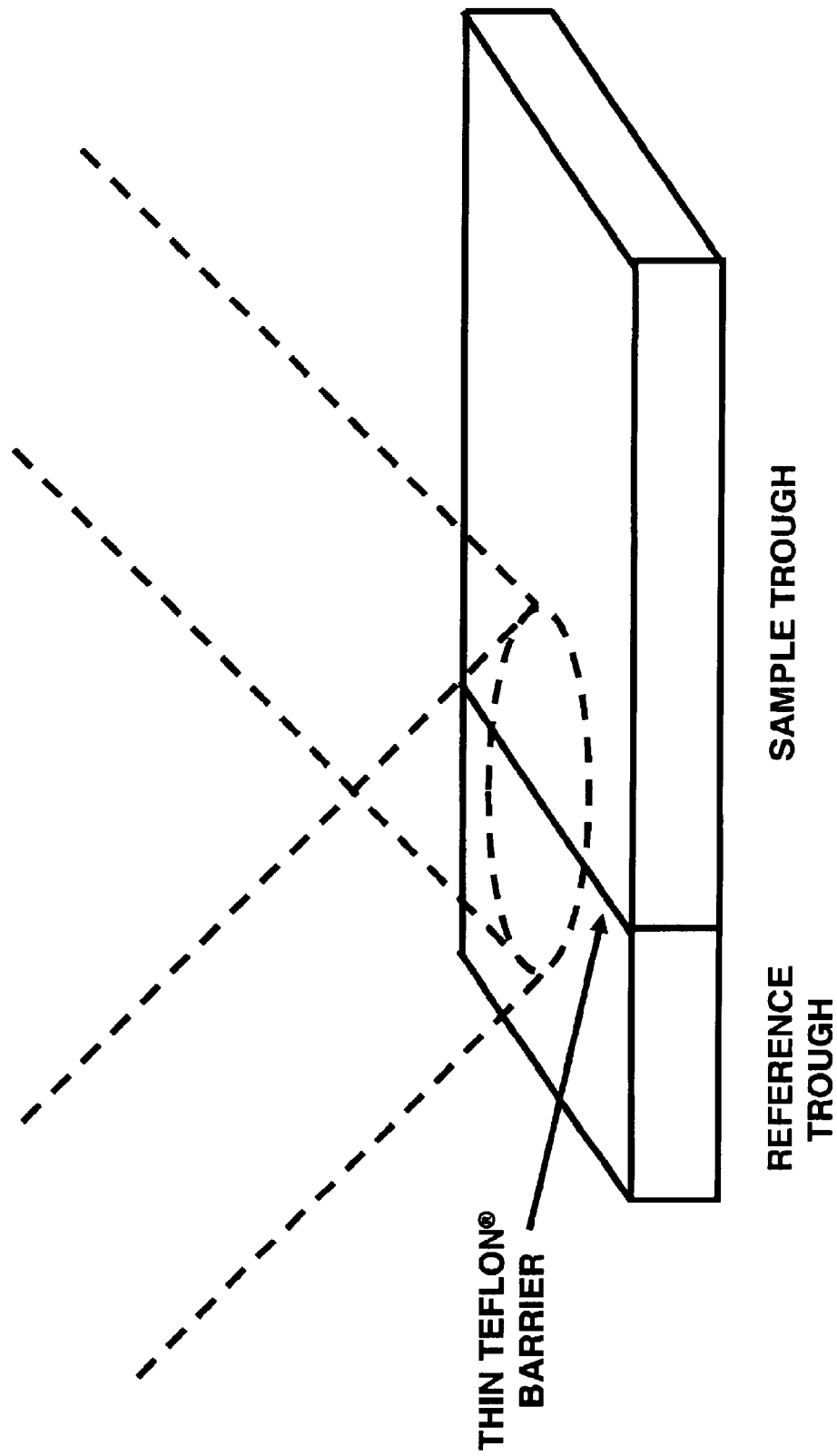
FIG. 6 shows a configuration suitable for real-time background correction.

In one aspect of this disclosure, a thin Teflon® barrier may be inserted in Langmuir film balance, so that two separate troughs are created, as seen in FIG. 6. The smaller trough may be used as a reference trough, while the larger tough may be used as a sample trough. The center of a relatively wide collimated infrared beam (e.g., 4 or 5 cm) may be reflected at the point where the two troughs are separated, i.e., at the thin Teflon® barrier.

Half of the IR beam would then be reflected by the reference subphase, while the other half of the beam would be reflected by the monolayer covered subphase. This results in separate "sample" (located at the top of the FPA, for example) and "reference" (located at the bottom of the FPA) spectral images projected on the FPA pixel array simultaneously (see FIG. 3C, for example). In this way, spectra obtained from the top rows of pixels would contain information on the Langmuir monolayer, while spectra obtained from the bottom rows of pixels will contain data from the substrate or reference surface, which could be, for example, water. A ratio of these two spectra at each wavelength will provide an absorbance spectrum, with the water vapor completely compensated.

In another aspect, polarized infrared spectra may readily be obtained by measuring the sample, e.g., a film, through polarizing elements using transmission or reflection of the IR beam, and then immediately directing the beam through a dispersive element. Alternatively, an emission may be split in a beam splitter (not shown), and then each split beam could be passed through two different, orthogonally polarized elements in respective optical paths, and through the sample or samples, to determine polarization-specific information.

Each polarized beam would then be dispersed by the optically dispersive element, i.e., the grating or prism. This would result in two orthogonally polarized beams being imaged on different rows of the FPA detector simultaneously, resulting in two separate polarized IR spectra.

Hence, polarized infrared spectra would then be available from the same place on the film at the same point in time, allowing determination of time-resolved dichroic ratios, for example.

Four spectral images (s-polarized reference, p-polarized reference, s-polarized sample and p-polarized sample) may be simultaneously projected onto the FPA. Orientation values could then be determined by comparing measured dichroic ratios with theoretical dichroic ratios obtained from simulations or handbooks, for example.

Further, for thin films, e.g., Langmuir films, time-resolved measurements in the sub-millisecond time regime may be obtained during the recording of a pressure area isotherm for polymers of interest by using signal averaging. The PAIR instrument's multiple spectral image capability allows higher intensity sources to be used to collect both spolarized and p-polarized spectra (reflectivity is significantly higher for s-polarized radiation than for p-polarized radiation) of monolayers during compression, thereby providing a continuous molecular picture of the development of order and orientation at all points along the isotherm.

Figure 7:
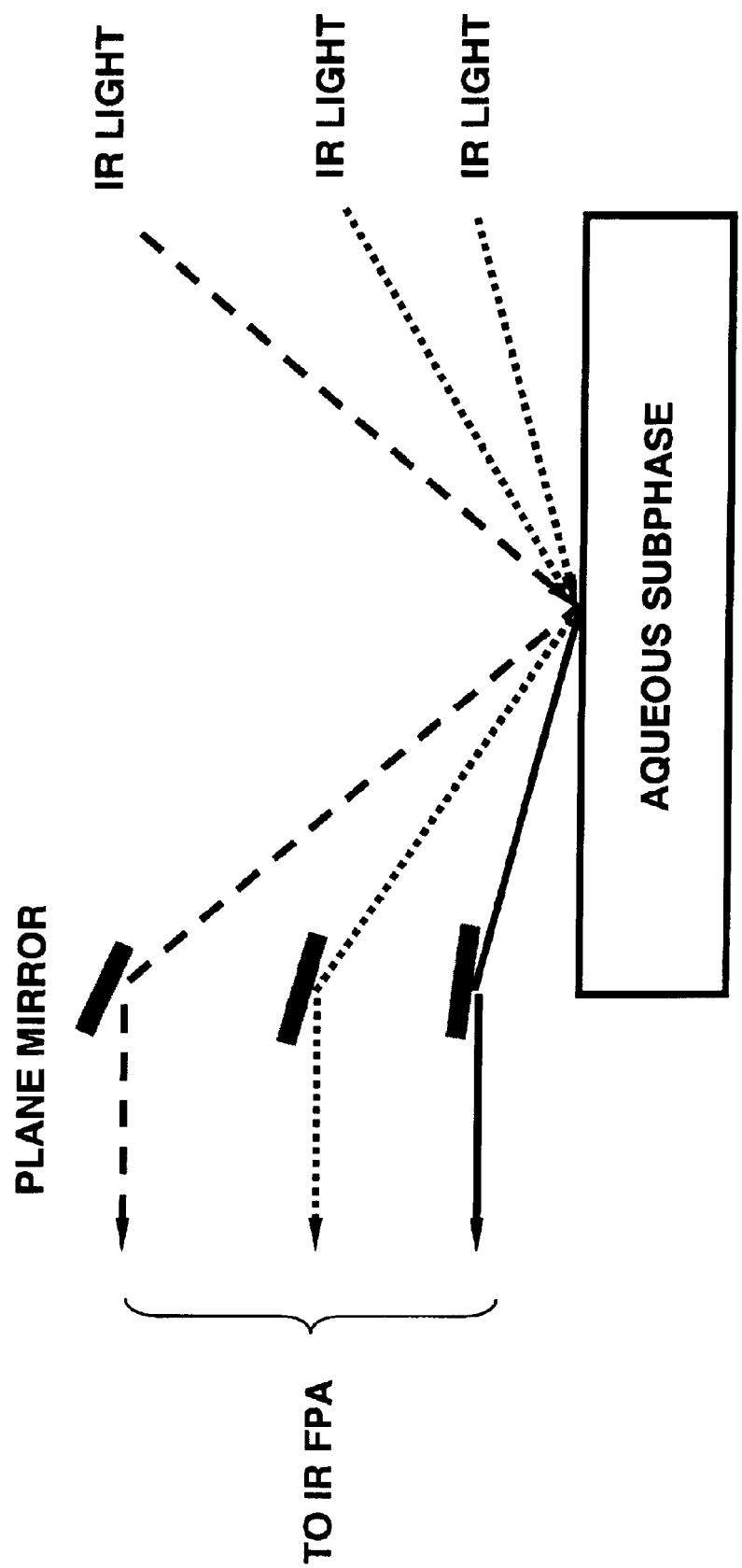
FIG. 7 shows an arrangement suitable for measuring multiple angles of incidence of IR radiation reflected from a surface.

In another aspect of disclosure using the PAIR spectrograph, external reflection measurements using multiple angles of incidence may simultaneously be made. A diagram of the arrangement is shown in FIG. 7, where small mirrors or optical fibers may be used to simultaneously collect multiple IR beams produced by multiple IR light sources. The separate infrared beams are directed to different areas of the entrance slit of an aperture portion of the instrument. This process ultimately produces multiple spectral images in different locations on the FPA, where each image corresponds to a different angle of incidence. Accurate molecular orientations of Langmuir monolayers may be determined using multiple angles of incidence. This additional capability of the PAIR instrument provides more accurate determination of molecular orientations in the investigation of Langmuir polymer monolayer characteristics.

In a further aspect of this disclosure, molecular orientations of thin films using polarized infrared spectra of the thin films may be determined. There are known techniques for doing so, however, for IR external reflection measurements from dielectric substrates, a knowledge of the anisotropic IR optical constants (e.g., index of refraction and extinction coefficient) is required. This information is often difficult to obtain.

Historically, there have been attempts to obtain anisotropic refractive indices using IR ellipsometry. The use of this technique has been typically limited to the determination of optical constants of very simple molecules, whose dimensions and orientation could be easily deduced from a model. Other methods use external reflection, attenuated total reflection (ATR), or transmission IR spectrometry to obtain optical constants.

More accurate IR spectroscopic methods have exploited the interdependence of the refractive index and the extinction coefficient via the Kramers-Kronig relationship along with the Fresnel equations to obtain the optical constants. Unfortunately, these methods often require a number of assumptions that can affect the reliability of the resulting complex refractive indices. This point is underscored by the fact that many researchers have used isotropic optical constants obtained from literature data, measured in bulk, that can further compromise the reliability of orientation measurements. It is clearly desirable to have a reliable technique for determining infrared optical constants that uses the same infrared spectrometer employed in the thin film analysis.

Figure 8:
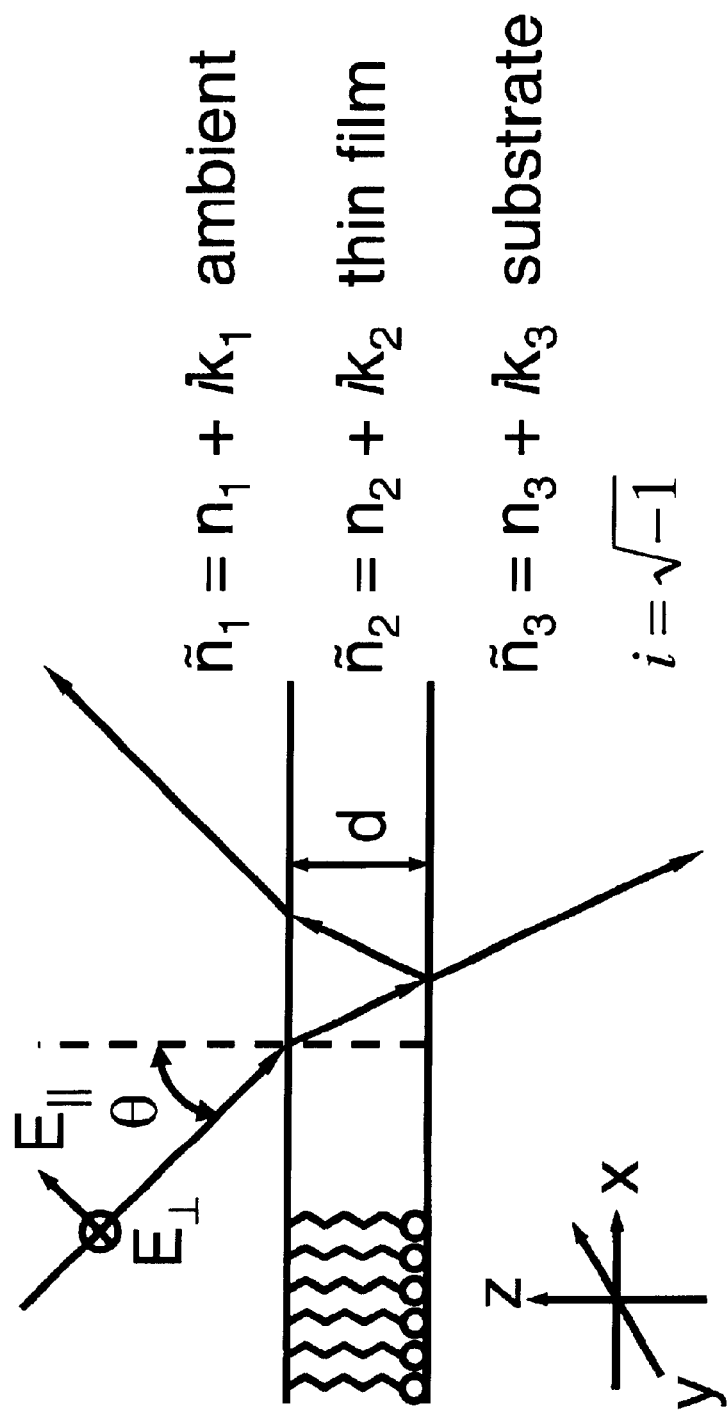
FIG. 8 depicts a stratified three-phase system representative of a thin film on a substrate.

With this in mind, the PAIR spectrograph of this disclosure may be applied to determine the anisotropic optical constants of the thin films. From an optics perspective, a monolayer film adsorbed on a dielectric substrate can conveniently be considered as a stratified three-phase system, such as that shown schematically in FIG. 8. The optical properties of the $j^{th}$ phase are characterized by the complex refractive index $\tilde{n}_j$ where $n_j$ is the real refractive index and $k_j$ is the absorption coefficient, i.e., $\tilde{n}_j=n_j+ik_j$, where $i=\sqrt{-1}$.

The film thickness is represented by d, which may be as small as one molecule, i.e., a monolayer. When the values $\tilde{n}_1$, $\tilde{n}_3$ and d are known, a PAIR spectrograph can be used to determine $n_2$ and $k_2$, i.e., the optical constants of the monolayer film. Film thickness is easily determined with a known visible ellipsometer, while $\tilde{n}_1$ (air) and $\tilde{n}_3$ (atypical dielectric substrate, for example) have known values.

Figure 9:
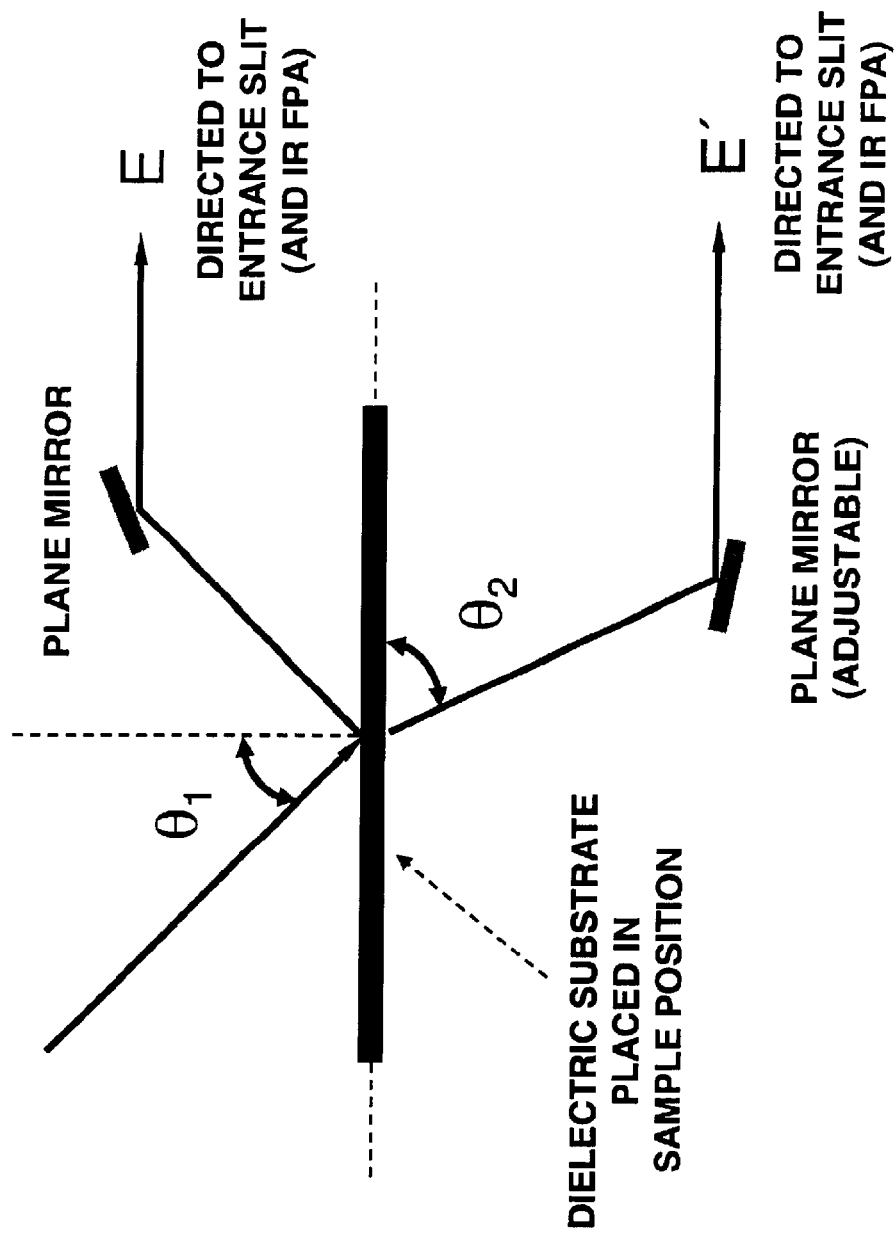
FIG. 9 shows an arrangement suitable for reflection/refraction measurement used in determining optical constants of a thin film.

FIG. 9 shows reflection and refraction of infrared radiation that is incident on a dielectric substrate, where B is the intensity of the reflected radiation (at a given frequency); E' is the intensity of the transmitted (refracted) radiation; $\theta_1$ is the angle of reflection, which is equal to the angle of incidence and is easily measured, and $\theta_2$ is the angle of refraction. With this disclosure, it is possible to measure B, E' and $\theta_2$. The angle $\theta_2$ may be measured using the following procedure.

First, a clean dielectric substrate is placed horizontally in the sample position (see FIG. 9). An arbitrary IR light source may be transmitted through the dielectric substrate at a known angle relative to the surface normal, where it then strikes the FPA at a specific, known area, "A" (not shown). The same dielectric substrate, now with an adsorbed monolayer film on it, is then placed in the sample position. The plane mirror is then rotated until light strikes the same area, "A", of the FPA. By accurately measuring the amount of mirror rotation necessary to return the transmitted IR beam back to area "A", the angle of refraction can be determined.

Once the values of B, E', $\theta_1$, $\theta_2$, $\tilde{n}_1$, $\tilde{n}_3$, and d are all known for several angles of incidence, the optical constants of the monolayer film, ($n_2$ and $k_2$) can be determined using the Fresnel equations and a known iterative procedure. Using multiple angles of incidence $\theta_1$ improves the accuracy of these determinations.

Figure 10:
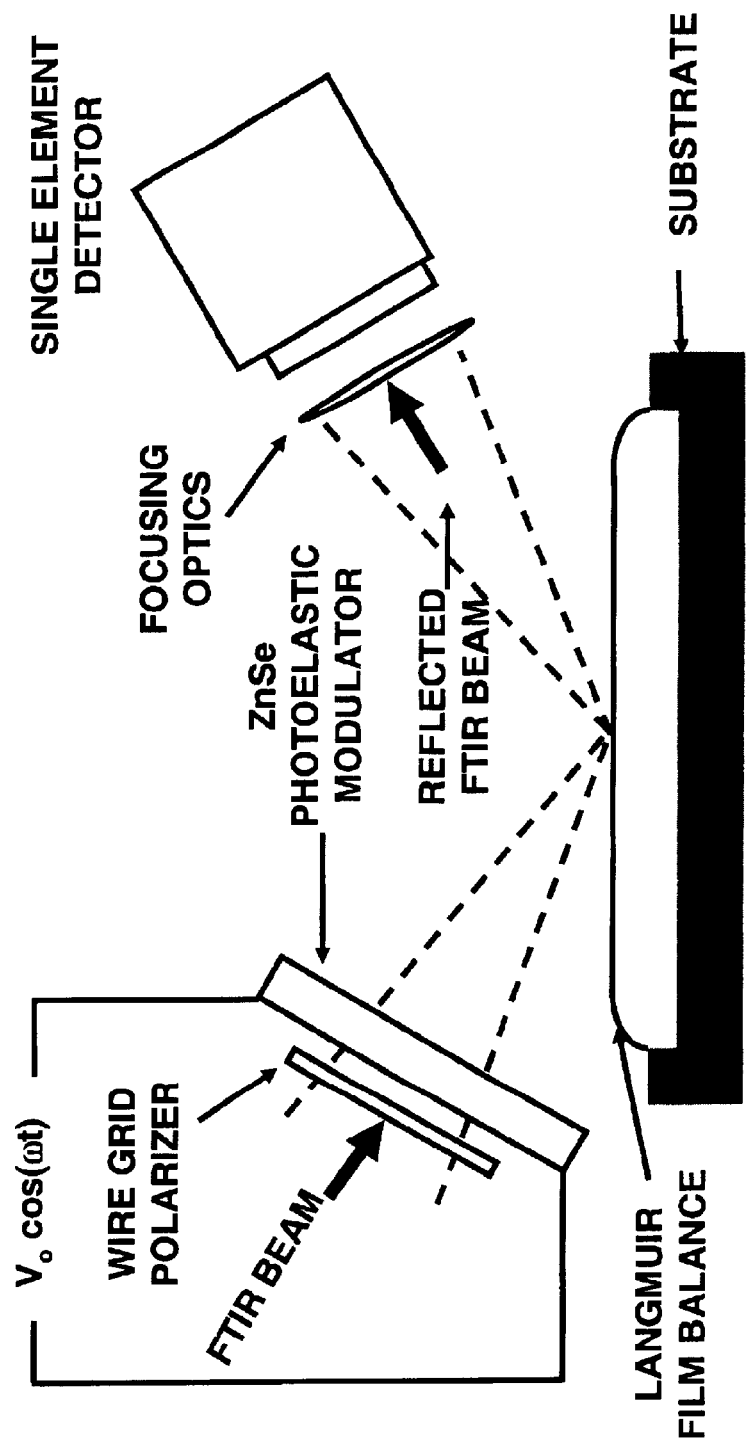
FIG. 10 shows an arrangement for conventional Polarization Modulation Infrared Reflectance-Absorbance Spectroscopy (PM-IRRAS)

The spectroscopy community and segments of industry alike are also faced with the problem of compensating for water vapor in the optical path. There are a variety of ways to minimize the problem of water vapor compensation affecting the measurement of sample spectra. For example, and with reference to FIG. 10, conventional polarization modulation infrared reflectance-absorbance spectroscopy (PM-IRRAS), using FTIR is used.

In conventional PM-IRRAS, the initially polarized incident FTIR light beam (via a wire grid polarizer, for example) undergoes a fast modulation between two orthogonal polarization directions via a photoelastic modulator. The detected signal passes through a two-channel electronic system, and is mathematically processed to give a differential reflectivity spectrum. Because of the fast polarization modulation, the PM-IRRAS differential reflectivity spectrum signal is essentially devoid of all polarization-independent signals, such as strong water vapor absorptions which are isotropic, instrumental drifts, and fluctuations in signal strength. However, this approach still relies upon the moving part and calculation-intensive Fourier Transform approach, which this disclosure specifically disfavors.

In another aspect of this disclosure directed, at least in part, to the above-identified problem of accounting for the presence of water vapor, and with reference to FIG. 11, a non-interferometric PAIR arrangement for Planar Array Infrared Reflectance-Absorbance Spectroscopy (PA-IRRAS) for measuring an orientation of a thin film on a substrate includes an IR source; two fixed, orthogonal polarizers 335, 336; a PAIR detector as previously described and illustrated, including a processor and a display.

The orthogonally polarized beams are reflected from the thin film, and detected by the PAIR detector. The processor then calculates a differential reflectivity spectrum based upon analysis of the two orthogonally polarized signals received by the PAIR detector. The differential spectrum is substantially free of any polarization-independent signals including isotropic water vapor absorptions, instrumental drifts, and signal fluctuations, because these effects are essentially canceled out by the differential technique. The differential reflectivity spectrum may be further used to determine a molecular orientation of the thin film. The polarization modulator may be a photoelastic modulator, and the FPA could be an InSb FPA, an MCT FPA, or a microbolometer FPA, for example.

The application and method of this disclosure has wide applicability to a variety of industrial and environmental processes, as discussed above, including measuring characteristics of thin films, including optical constants.

Some further applications include a method to measure the thickness, the chemical structure and orientation of coatings (solid, liquid, chemically bound, physically adsorbed) on solid surfaces, including but not limited to semiconductors, metals and dielectrics.

For example, in modern materials processing utilized in device manufacturing, subtle differences in the processed materials on a molecular level can determine the success or failure of a specific procedure. Molecular parameters such as crystalline order, chain orientation, and hydrogen bonding strength can have important effects on the functionality of the final devices. For example, liquid crystal displays used in notebook computers rely on the chain orientation of the polymer coating used on the glass templates to define the "off" orientation of the liquid crystal molecules, which act as a light modulator.

The orientation of such polymer chains, however, is produced by a "buffing" process during which a piece of velour cloth is used to rub the polymer-coated glass in a given direction in order to induce chain orientation. Although it is well known that the yield of a flat panel display manufacturing line is critically dependent on a successful buffing process, there is no monitoring process used during the various manufacturing stages that can assess the chain orientation induced by buffing before final assembly is completed. Hence glass templates with bad LC aligning properties are not removed from the assembly line until the manufacturing process is completed. The cost of discarding failed fully assembled displays is several times higher than that of removing polymercoated-and-buffed glass plates with poor alignment properties. The main difficulty in realizing this more efficient quality control process is that, until now, there was no reliable detection method that can survive the aggressive operating conditions found in a manufacturing plant.

Process methods such as scanning probe microscopy and x-ray diffraction, for example, can be destructive in nature, requiring long data collection times and removal of samples from the production line. Consequently, the realtime statistics needed for a successful on-line process monitoring method cannot be achieved with conventional techniques. The disclosed apparatus and method can non-destructively monitor processes in real-time, for example, information about chain orientation of large area samples can be obtained in situ after the buffing process is completed.

Further, because of the multi-beam approach, different sample areas of the same sample or different samples can be simultaneously monitored, while compensating for background spectra and component aging, essentially in real time.

The present inventors have been involved in the study of liquid crystal alignment using different organic, inorganic and polymer surfaces, and have shown that the ordering, orientation, morphology, and topography of the template surface plays an important role in the final LC orientation.

This information will be readily accessible to the flat panel display industry with the use of the portable infrared spectrometer disclosed here.

An environmental application of IR spectroscopy in an aqueous environment, for example on a lake, river, or on the ocean could be detection and measurement of oil or other contaminants on the surface using reflected IR energy to determine the presence or absence of specific functional groups.

In addition, because the IR spectrometer is highly mobile, it may be used as a water pollution monitor, capable of operation in the field as discussed above. The spectral coverage of this disclosure will detect the spectral features in the fingerprint region for most aromatic pollutants. Since the IR bands (1600–1750 cm$^{-1}$) assignable to water will not interfere with the pollutants'signal in this spectral range, bulk analysis of wastewater in the field is also possible with this instrument.

Another application, discussed in connection with one aspect, above, involves IR spectroscopy on thin films. Many of the optical, mechanical and aging properties of polymers are a direct function of the order, orientation, and morphological development, which occurs during processing. Ironically little, if any, understanding exists on the structural development of orientation and order at the time when polymers are formed into thin films. The ability to structurally characterize the nature of polymer chain organization by real-time IR spectroscopic methods would allow the optimization of processing protocols providing eventual control of the desired amount of crystallization and orientation relative to the direction of micro mechanical deformation.

In many cases, this is simply manifested by specific IR bands that can be attributed to either trans or gauche bonds, and crystalline or amorphous material. Following both the intensity and the frequency of IR bands as processing (heating, stretching, cooling) of thin films occurs will allow us to follow the molecular development of orientation and crystal morphology as it occurs.

Although many studies on poly(ethylene) (PE) films and fibers have been done, the information provided is usually obtained both before processing, and after deformation, heating, etc., has been completed. Providing spectroscopic information in different spatial regions and in real-time is possible with the disclosed IR instrument. Depending on the spectral range of the focal plane array chosen, it is possible to investigate the development of crystallinity using the 1460–1470 cm$^{-1}$ (doublet) CH$_2$ scissors vibration, and the 720–730 cm$^{-1}$ (doublet) CH$_2$ rocking vibration, which are characteristic of the orthorhombic unit cell. Furthermore, since the transition moments of the CH$_2$ rocking components at 730 and 720 cm$^{-1}$ are parallel to the "a" and "b" axes of the unit cell ("c" is along the chain axis) respectively, it should also be possible to determine the extent of biaxial orientation which is introduced in the drawing process by following the relative intensities of the 730 and 720 cm$^{-1}$ bands in the polarized IR beam during processing.

In addition, since both sets of bands (rocking and scissors) are highly polarized perpendicular to the polymer chain axis, their intensity can also be used to provide information on axial orientation related to the direction of mechanical deformation. Likewise the CH stretching vibrations located at 2920 cm$^{-1}$ (asymmetric CH$_2$stretch) and 2850 cm$^{-1}$ (symmetric CH$_2$ stretch) are strongly polarized out of the plane of the carbon backbone and in the plane of the carbon backbone respectively. Hence these vibrations can also be used to determine the extent of "a" and "b" axis orientation in biaxially oriented films.

Unlike Raman spectroscopy where the intensities depend on changes in polarizabilities, making the interpretation of induced orientation less straightforward, IR intensities depend on the change in dipole moment (for a particular vibrational mode), and hence provide a more direct assessment of chain orientation, provided the direction of the orientation of the change in dipole moment is known, relative to the polymer chain axis. In the case of PE, these are well known, and PE is an appropriate polymer on which to conduct IR spectroscopy.

Another application is to measure a series of poly(ester) thin films. Although a number of studies on poly(ethylene terephthalate) (PET) films pre- and post-processing have appeared in the literature, no studies on PET during processing have been reported. In addition, little work has appeared on structurally related poly(ethylenenaphthalate) (PEN). Since the primary commercial market for PEN is now specialty films, because of its improved (relative to PET) thermal and dielectric properties, an understanding of the effect of various processing parameters on properties would be both fundamentally important and timely.

In previous studies of PET after stretching, it has been shown that bands at 973 and 1041 cm$^{-1}$, previously assigned to trans and gauche conformations of the —OCH$_2$ CH$_2$O— groups, show a considerable change in intensity (973 cm$^{-1}$ also shifts in frequency) after the application of stress. This suggests that stress transforms gauche bonds into trans, although this evidence alone did not indicate that the overall sample crystallinity had increased. This required the use of the 848 cm$^{-1}$ CH$_2$ rocking vibration characteristic of trans conformers in the crystalline regions which was also followed as a function of stress and found to increase as the 973 cm$^{-1}$ trans band increased.

Similar behavior was also observed for the 1386 cm$^{-1}$ CH$_2$ wagging mode which has also been observed to be characteristic of trans bonds in the crystalline regions of PET. Since the —OCH$_2$CH$_2$O— groups are common linkages between the aromatic groups in both polyester chains, monitoring the intensity and frequency changes of the 973, 1041, 848 and 1386 cm$^{-1}$ bands so as to understand the effect of processing parameters on the development of orientation, all trans content and crystallinity in both PET and PEN films. In addition, changes in crystallization and orientation in PET and PEN can also verified by following the CH stretching modes at 2870 and 2850 cm$^{-1}$ while orientation alone can be followed using the C=O overtone vibration at 3200 cm $^{-1}$.

Further industrial applications of the disclosed apparatus include a method to measure and detect the thickness, either in transmission or reflection, the chemical structure and orientation of coatings/films (solid, liquid, chemically bound, physically adsorbed) on liquid surfaces, including but not limited to water, oil and other solvents.

Although discussion of aspects of this disclosure have been directed to determining IR spectral information, the method and system of this disclosure is not limited merely to such a narrow implementation. For example, this disclosure may also be applicable to the above-discussed industrial and environmental processes, and may further be incorporated into a control system in a batch production line to control one or more physical attributes, such as a polymer film thickness, or in semiconductor processing, for example, while measuring multiple samples simultaneously, and while compensating for background emissions.

It will be obvious that this disclosure may be varied in many ways. For example, the specific optical components may be varied, as may their particular location with respect to the sample volumes or IR sources. Such variations are not to be regarded as a departure from the spirit and scope of this disclosure, and all such modifications as would be obvious to one skilled in the art are intended to be included within the scope of the following claims. The breadth and scope of the invention is therefore limited only by the scope of the appended claims and their equivalents.

What is claimed is:

1. An apparatus for simultaneously spatially multiplexing IR spectral information for each of a plurality of samples, comprising:
   at least one IR light source;
   at least one sample holder which positions the plurality of samples in an optical path;
   an optically dispersive element in the optical path,
   wherein an emission from the at least one IR light source interacts with each of the plurality of samples along the optical path to form a corresponding plurality of sample emissions,
   said plurality of sample emissions interacting with the optically dispersive element to form a corresponding plurality of dispersed sample light beams, each of said plurality of dispersed sample light beams corresponding to a respective one of the plurality of samples; and
   an IR FPA detector arranged in the optical path, said IR FPA detector having multiple pixels arranged in plural rows and columns,
   wherein the IR FPA detector detects the corresponding plurality of dispersed sample light beams and provides at least one output which represents the IR spectral information for each of the plurality of samples.

2. The apparatus of claim 1, wherein the optically dispersive element is a diffraction grating.

3. The apparatus of claim 1, wherein the optically dispersive element is a prism.

4. The apparatus of claim 3, wherein the optically dispersive element is a Pellin-Broca prism substantially transparent to IR wavelengths.

5. The apparatus of claim 1, wherein the optically dispersive element is adjustable, and a range of wavelengths included in the corresponding plurality of dispersed sample light beams projected onto the IR FPA detector is determined by adjusting an angle of incidence between the emission from the IR light source and a surface of the optically dispersive element.

6. The apparatus of claim 1, wherein the emission from the IR light source interacts with a background reference environment arranged along the optical path to provide a background reference emission,
   said background reference emission interacting with the optically dispersive element to form a dispersed background reference light beam,
   wherein the IR FPA detector detects the dispersed background reference light beam.

7. The apparatus of claim 6, further comprising a processor which receives the at least one output and a signal representing the dispersed background reference light beam, wherein said processor, essentially in real-time, determines compensated IR spectral information for each of the plurality of samples by compensating for the background reference environment.

8. The apparatus of claim 1, further comprising a first polarizer in the optical path, wherein at least one of the corresponding plurality of sample emissions passes through the first polarizer to form a first polarized sample emission.

9. The apparatus of claim 8, further comprising a second polarizer in the optical path, wherein at least one of the corresponding plurality of sample emissions passes through the second polarizer to form a second polarized sample emission orthogonal to the first polarized sample emission,
   wherein the first and second polarized sample emissions interact with the optically dispersive element to form first and second dispersed polarized light beams,
   wherein the IR FPA detector detects the first and second dispersed polarized light beams.

10. The apparatus of claim 9, wherein the first polarized sample emission has a polarization perpendicular to a polarization of the second polarized sample emission.

11. The apparatus of claim 9, wherein the first and second dispersed polarized light beams are used to determine a molecular orientation of a polymer film.

12. The apparatus of claim 1, wherein the IR FPA detector detects each of the corresponding plurality of dispersed sample light beams on spatially separated areas of the IR FPA detector.

13. The apparatus of claim 1, wherein the IR FPA detector simultaneously detects the corresponding plurality of dispersed sample light beams.

14. The apparatus of claim 1, wherein the at least one output determines the IR spectral information for each of the plurality of samples at a same instant in time.

15. The apparatus of claim 1, wherein the IR FPA detector comprises InSb.

16. The apparatus of claim 1, wherein the IR FPA detector comprises MCT.

17. The apparatus of claim 1, wherein the IR FPA detector comprises a microbolometer.

18. The apparatus of claim 1, wherein the at least one output from the IR FPA detector includes a plurality of summed pixel outputs at each of a plurality of wavelengths contained in the dispersed light beam,
   wherein the plurality of summed pixel outputs at one of the plurality of wavelengths improves a signal-to-noise-ratio of a signal representing an intensity of said one of the plurality of wavelengths.

19. The apparatus of claim 1, wherein a plurality of IR FPA detector pixel outputs corresponding to at least one of a plurality of wavelengths contained in at least one of the corresponding plurality of dispersed sample light beams are summed together to improve a signal-to-noise-ratio of a signal representing an amplitude of the at least one of a plurality of wavelengths.

20. The apparatus of claim 1, wherein the IR FPA detector is partitioned into multiple segments each containing a different subset of the multiple pixels,
   wherein each of the corresponding plurality of dispersed light beams are projected onto an associated one of the multiple segments.

21. The apparatus of claim 20, wherein said each of the corresponding plurality of dispersed sample light beams are projected onto the IR FPA detector such that a row direction on the IR FPA detector is essentially aligned with a dispersion direction of said each of the corresponding plurality of dispersed sample light beams, wherein each column of the IR FPA within each of the multiple segments corresponds to a particular wavelength of light in an associated one of the plurality of dispersed sample light beams.

22. The apparatus of claim 20, wherein, within at least one of the multiple segments, an output from one pixel in each of a plurality of rows are added together along one column of the FPA to improve a signal-to-noise-ratio of a signal representing an intensity of an associated wavelength of light.

23. The apparatus of claim 20, wherein dispersed sample light beams associated with different spatial sections of one of the plurality of samples are projected onto two or more of the multiple segments.

24. The apparatus of claim 20, wherein different wavelengths are represented within at least two of the multiple segments.

25. The apparatus of claim 24, wherein dispersed sample light beams associated with different spatial sections of one of the plurality of samples are each projected onto different ones of said at least two of the multiple segments.

26. The apparatus of claim 1, wherein the IR FPA detector detects light having a wavelength at least in a mid-IR band.

27. The apparatus of claim 1, wherein at least one of the plurality of samples includes a background target having an analyte therein,
wherein the analyte reacts to a specific type of sample to produce an IR absorption change in the background target.

28. The apparatus of claim 27, wherein the analyte is a bio-specific reagent reactive to one or more biohazardous materials.

29. The apparatus of claim 28, further comprising an audible or visual alarm, or both, which are activated when the bio-specific reagent reacts to said one or more biohazardous materials.

30. The apparatus of claim 1, wherein said optical path includes at least one optical fiber.

31. The apparatus of claim 30, wherein said optical path includes a plurality of optical fibers.

32. The apparatus of claim 30, wherein said at least one optical fiber is a multimode fiber.

33. The apparatus of claim 30, wherein said at least one optical fiber propagates light in a mid-IR band.

34. The apparatus of claim 1, wherein said at least one sample holder includes a plurality of sampling accessories, each of said plurality of sampling accessories positioning a different sample volume in the optical path,
wherein the apparatus simultaneously determines IR spectral information for each of the different sample volumes.

35. The apparatus of claim 1, wherein said at least one sample holder is configured to provide an optical path for each of the plurality of samples which is suitable for detection of an IR absorption phenomena within said optical path.

36. The apparatus of claim 1, further comprising a plurality of optically dispersive elements for forming a plurality of dispersed light beams each corresponding to a different sample,
wherein each of said plurality of dispersed light beams is projected onto a different spatial area on the IR FPA detector.

37. The apparatus of claim 1, further comprising:
a display for displaying an IR spectrograph for one or more of the plurality of samples; and
means for controlling the IR FPA detector and the display.

38. The apparatus of claim 37, wherein the means for controlling the IR FPA detector and the display includes a personal computer.

39. The apparatus of claim 1, wherein IR FPA detector further comprises an IR camera.

40. The apparatus of claim 1, wherein the emission from the at least one IR light source is transmitted through each of the plurality of samples along the optical path.

41. The apparatus of claim 1, wherein the emission from the at least one IR light source reflects from each of the plurality of samples along the optical path.

42. A real-time, non-interferometric apparatus using IR absorption phenomena and no moving parts during operation to simultaneously perform chemical analysis in a plurality of sample volumes, the apparatus comprising:
a broadband light source;
at least one sampling accessory for positioning the plurality of sample volumes so that at least a portion of light emitted from the broadband light source interacts with each of the plurality of sample volumes;
adjustable means for optically dispersing the at least a portion of light interacted with each of the plurality of sample volumes to obtain a plurality of corresponding dispersed sample beams;
a two-dimensional IR detector array having a plurality of detector elements arranged in rows and columns, optical coupling means for coupling the plurality of corresponding dispersed sample beams onto the two-dimensional IR detector array; and
processor means for controlling the two-dimensional IR detector array and providing non-interferometric chemical analysis of said plurality of samples based at least upon an IR absorption spectrum in one or more particular wavelength regions,
wherein each of the plurality of corresponding dispersed sample beams are projected on multiple rows in a different area of the two-dimensional IR detector array, and corresponding column detector elements in each of the multiple rows are added together within each different area of the two-dimensional IR detector array to determine an intensity of an IR spectral component at a particular wavelength in real time,
wherein a signal-to-noise-ratio of a signal representing the intensity of the IR spectral component at the particular wavelength is increased by adding the corresponding column detector elements in each of the multiple rows.

43. The apparatus of claim 42, wherein the adjustable means for optically dispersing the at least a portion of light passed through each of the one or more samples is a diffraction grating having an adjustable angle of incidence with respect to incident light projected thereon.

44. The apparatus of claim 42, wherein the adjustable means for optically dispersing the at least a portion of light passed through each of the one or more samples is a Pellin-Broca prism having an adjustable angle of incidence with respect to incident light projected thereon.

45. The apparatus of claim 42, wherein the at least a portion of light emitted from the broadband light source is transmitted through said each of the plurality of sample volumes.

46. The apparatus of claim 42, wherein the at least a portion of light emitted from the broadband light source is reflected from said each of the plurality of sample volumes.

47. The apparatus of claim 42, wherein the optical coupling means includes one or more optical fibers.

48. The apparatus of claim 42, wherein the two-dimensional IR detector array is an InSb focal plane array.

49. The apparatus of claim 42, wherein the two-dimensional IR detector includes MCT.

50. The apparatus of claim 42, wherein the processor means is a personal computer.

51. A method of performing chemical analysis of the plurality of samples by determining an IR absorption spectrum of each of the plurality of samples using the apparatus of claim 42, the method comprising:
projecting at least a portion of an emission of the broadband light source onto the plurality of sample volumes;
interacting the at least a portion of an emission of the broadband light source with the plurality of sample volumes;
providing a corresponding plurality of sample emissions to an optically dispersive element;
forming a plurality of corresponding dispersed sample beams;
optically coupling the plurality of corresponding dispersed sample beams onto the two-dimensional IR detector array,
wherein each of the plurality of corresponding dispersed sample beams are projected on multiple rows in a different area of the two-dimensional IR detector array;
non-interferometrically processing, within each different area of the two-dimensional IR detector array, an output from each detector in a plurality of rows of detectors,
wherein each column of detectors represents a particular wavelength within each different area;
determining the IR absorption spectrum of each of the plurality of samples by evaluating a processed output from said each detector; and
at least partially analyzing a chemical makeup of each of the plurality of samples by comparing the processed output to one or more reference standards.

52. The method of claim 51, further comprising maintaining the broadband light source, the optically dispersive element, and the two-dimensional IR detector array relatively motionless at least with respect to each other at least during said steps of projecting, interacting, coupling, forming, and optically coupling.

53. The method of claim 51, further comprising increasing a signal-to-noise-ratio by co-adding a plurality of detector outputs in each column within said each different area.

54. The method of claim 51, wherein said optical coupling step includes fiber optic coupling.

55. The method of claim 51, wherein said projecting includes fiber optical coupling the at least a portion of the emission of the broadband light source into the plurality of sample volumes.

56. The method of claim 51, further comprising:
interacting the at least a portion of an emission of the broadband light source with a bio-specific reagent in a background reference sample;
detecting an IR absorption change in the background reference sample resulting from the bio-specific reagent reacting with a biohazardous material having a specific functional group; and
enabling an alarm if the IR absorption change in the background reference sample is detected.

57. The method of claim 51, further comprising determining, from the IR absorption spectrum of one or more of the plurality of samples, at least one physical attribute of the one or more of the plurality of samples,
wherein the at least one physical attribute is continuously determined essentially in real-time.

58. The method of claim 57, wherein said determining at least one physical attribute includes determining a molecular orientation of one of the plurality of samples.

59. The method of claim 58, wherein said determining a molecular orientation of said one of the plurality of samples is accomplished, at least in part, by comparing two orthogonally polarized sample emissions associated with said one of the plurality of samples.

60. The method of claim 59, wherein said one of the plurality of samples is a polymer film.

61. The method of claim 57, wherein said determining at least one physical attribute includes measuring a thickness of a film in real-time.

62. A method of simultaneously determining an IR spectrum of a plurality of sample volumes using a non-interferometric apparatus capable of operating using no moving parts, the method comprising:
providing an IR source;
positioning the plurality of sample volumes in an optical path;
interacting at least a portion of an emission of the IR source with the plurality of sample volumes along the optical path to form a plurality of sample emissions;
optically dispersing the plurality of sample emissions to form a corresponding plurality of dispersed sample beams;
detecting each of the plurality of dispersed sample beams on spatially separated areas on a focal plane array having rows and columns of pixels thereon; and
simultaneously and non-interferometrically determining the IR spectrum of each of the plurality of sample emissions by evaluating a combined output from each spatially separated area of the focal plane array,
wherein each column of pixels in one of the spatially separated areas represents a wavelength contained within an associated one of the plurality of sample emissions.

63. The method of claim 62, further comprising adjusting an optical dispersion of the plurality of sample emissions to control a range of wavelengths in the plurality of dispersed sample beams.

64. The method of claim 62, further comprising increasing a signal-to-noise-ratio by co-adding a plurality of pixel outputs in said each column of pixels in said one of the spatially separated areas.

65. The method of claim 62, further comprising:
simultaneously evaluating a reference spectrum of an environmental background; and
correcting the IR spectrum of each of the plurality of sample to account for the reference spectrum of the environmental background.

66. The method of claim 62, further comprising:
simultaneously evaluating a spectrum of the IR source; and
correcting the IR spectrum of each of the plurality of sample to account for the spectrum of the IR source.

67. The method of claim 66, further comprising:
simultaneously evaluating a reference spectrum of an environmental background; and
correcting the IR spectrum of each of the plurality of sample to account for the reference spectrum of the environmental background.

68. The method of claim 62 further comprising:
processing the IR spectrum of each of the plurality of sample emissions to identify one or more signature functional groups in the plurality of sample volumes; and enabling an alarm if said one or more signature functional groups are found in any one of the plurality of sample emissions.

69. The method of claim 68 further comprising:
providing a background target having a bio-specific reagent thereon; and
reacting the bio-specific reagent with a sample volume containing said one or more signature functional groups.

70. An apparatus for simultaneously collecting, processing, and displaying IR spectral information for one or more samples, comprising:
a plurality of IR light sources;
at least one optically dispersive element;
a plurality of optical paths;
an IR FPA;
processing means for processing an output of the IR focal plane array and determining the IR spectral information; and
display means for displaying the IR spectral information,
wherein each of the plurality of IR light sources presents a different angle of incidence with respect to the one or more samples,
wherein each of the plurality of optical paths directs an associated one of a plurality of reflected IR beams to a different spatial area on the IR FPA.

71. The apparatus of claim 70, wherein each of the plurality of IR light sources has a different intensity.

72. The apparatus of claim 70, wherein at least one of the plurality of optical paths includes a polarizing element.

73. The apparatus of claim 70, wherein at least one of the plurality of optical paths includes fiber optical coupling.

74. The apparatus of claim 70, wherein said processing means determines a molecular orientation of a polymer monolayer from IR spectral information determined from the different spatial areas on the IR FPA.

75. A method of determining anisotropic IR optical constants of a material, comprising:
providing a substrate;
projecting an IR light source onto a surface of the substrate at a non-perpendicular angle of incidence;
transmitting a first transmitted portion of the IR light source through the substrate;
coupling the first transmitted portion of the IR light source through an optical path and onto a first area on a FPA;
providing a film material on the substrate;
projecting the IR light source onto a surface of the film material at the non-perpendicular angle of incidence;
transmitting a second transmitted portion of the IR light source through the film material and the substrate;
coupling the second transmitted portion of the IR light source through the optical path onto a second area on the FPA;
rotating a mirror in the optical path to move the second area on the FPA so as to coincide with the first area on the FPA;
determining an angle of refraction within the film material by measuring an angle of rotation of the mirror.

76. The method of claim 75, further comprising computing a refractive index and an absorption coefficient of the film material.

77. The method of claim 75, wherein said providing a substrate includes providing a dielectric substrate having known optical properties.

78. The method of claim 75, wherein said providing a film material on the substrate includes providing a monolayer film adsorbed on the substrate.

79. The method of claim 75, further comprising projecting the IR light source onto a surface of the substrate at a plurality of non-perpendicular angles of incidence; and
determining the angle of refraction within the film material by measuring the angle of rotation of the mirror for each of the plurality of non-perpendicular angles of incidence.

80. The method of claim 75, further comprising projecting polarized IR radiation through the film material and the substrate;
determining directionally specific angles of refraction within the film material; and
computing directionally specific complex indices of refraction of the film material.

81. The method of claim 80, further comprising calculating an orientation of at least one molecular group in the film material.

82. An arrangement for measuring an orientation of a thin film on a substrate, the arrangement comprising:
an IR source;
two orthogonally polarized filters which receive an IR light beam from the IR source;
a PAIR detector; and
a processor,
wherein two orthogonally polarized IR beams emanating from the two orthogonally polarized filters are reflected from the thin film and detected by the PAIR detector,
wherein a differential reflectivity spectrum is calculated by the processor, and
wherein the differential reflectivity spectrum is substantially free of any polarization-independent signals including water vapor absorptions, instrumental drifts, and signal fluctuations.

83. The arrangement of claim 82, wherein the PAIR detector includes an InSb FPA.

84. The arrangement of claim 82, wherein the PAIR detector includes an MCT FPA.

85. The arrangement of claim 82, wherein the PAIR detector includes a microbolometer FPA.

86. The arrangement of claim 82, wherein the processor uses the calculated differential reflectivity spectrum to determine a molecular orientation of the thin film.

87. A method of determining an orientation of a thin film on a substrate, the method comprising:
providing an IR source;
producing two orthogonally polarized light beams from the IR source;
reflecting the two orthogonally polarized light beams from the thin film,
detecting the two reflected orthogonally polarized light beams with a PAIR detector; and
calculating a differential reflectivity spectrum in the processor using the two reflected orthogonally polarized light beams, wherein the differential reflectivity spectrum is essentially free of any polarization-independent signals including water vapor absorptions, instrumental drifts, and signal fluctuations.

* * * * *